US008562717B2

(12) United States Patent
Antonelli

(10) Patent No.: US 8,562,717 B2
(45) Date of Patent: Oct. 22, 2013

(54) METAL HYDRAZIDE MATERIALS

(76) Inventor: David Michael Antonelli, Cardiff (GB)

( * ) Notice: Subject to any disclaimer, the term of this patent is extended or adjusted under 35 U.S.C. 154(b) by 246 days.

(21) Appl. No.: 12/998,984

(22) PCT Filed: Dec. 22, 2009

(86) PCT No.: PCT/CA2009/001893
§ 371 (c)(1),
(2), (4) Date: Aug. 10, 2011

(87) PCT Pub. No.: WO2010/072002
PCT Pub. Date: Jul. 1, 2010

(65) Prior Publication Data
US 2011/0308971 A1 Dec. 22, 2011

Related U.S. Application Data

(60) Provisional application No. 61/193,780, filed on Dec. 23, 2008.

(51) Int. Cl.
*B01J 20/26* (2006.01)
*C07F 11/00* (2006.01)

(52) U.S. Cl.
USPC .......... 95/90; 502/526; 423/413; 206/7; 556/12

(58) Field of Classification Search
USPC .......... 95/90, 900; 96/108; 502/526, 400; 423/413, 648.1; 206/0.7; 556/12; 429/515
See application file for complete search history.

(56) References Cited

U.S. PATENT DOCUMENTS

| | | | |
|---|---|---|---|
| 7,491,263 B2* | 2/2009 | Wang et al. | 96/108 |
| 8,343,260 B2* | 1/2013 | Omary et al. | 95/116 |
| 2007/0217994 A1* | 9/2007 | Amendola et al. | 423/648.1 |
| 2010/0022791 A1* | 1/2010 | Ihm et al. | 556/51 |
| 2010/0186588 A1* | 7/2010 | Yaghi et al. | 95/127 |
| 2011/0071066 A1* | 3/2011 | Wagner et al. | 510/237 |
| 2012/0186449 A1* | 7/2012 | Yaghi et al. | 95/90 |

FOREIGN PATENT DOCUMENTS

| | | |
|---|---|---|
| JP | 2005/232222 | 9/2005 |
| JP | 2010/070546 | 4/2010 |

OTHER PUBLICATIONS

Ferguson, et al.; "Stepwise Reduction of Dinitrogen Occurring on Divanadium Model Compound: A Synthetic, Structural, Magnetic, Electrochemical, and Theoretical Investigation on the $[V=N=N=V]^{n+[n=4-6]}$Based Complexes"; S002-7863(97)01229-8 CCC 1997 American Chemical Society, 119(42), 10104-10115.
Cotton, FA et al. 'Advanced Inorganic Chemistry, 6th Edition'.
Latesky, SL et al., 'Synthetic and Mechanistic Aspects . . . Metal Centres', Journal of the American Chemical Society, 1985, 107, 5981-5987.

(Continued)

*Primary Examiner* — Frank Lawrence, Jr.
(74) *Attorney, Agent, or Firm* — Thorpe North & Western LLP

(57) ABSTRACT

The present invention provides the following new polymers which are useful for hydrogen storage: (i) a polymer comprising -[$MN_2$]— as a repeating unit, wherein M is selected from the group consisting Sc, Ti, V, Cr, Mn, Fe, Co, Zr, Nb, Mo, and mixtures thereof; and (ii) a polymer comprising -[$M_2N_3$]— as a repeating unit, wherein M is selected from the group consisting Sc, Ti, V, Cr, Mn, Fe, Co, Zr, Nb, Mo, and mixtures thereof.

39 Claims, 29 Drawing Sheets

(56) References Cited

OTHER PUBLICATIONS

Gambarotta, S et al., 'The Unusual Stability of Homoleptic Di- and Tetravalent Chromium Alkyls', Organometallics, 2002, 21, 3810-3816.

Yakowlewa, O et al., Doklady Akademii Nauk SSSR, 1974, 218 (3), 593-596.

Seidel, VW et al., 'Arylvanadium (III) Compounds, III. Preparation and Properties of Triaryl Vanadium Complexes', Z. Anorg. Allg. Chem. 1977, 435, 146-152.

Jacob, VK et al., 'Contributions to the Chemistry . . . Vanadium and Chromium Acetylacetonates', Z. Anorg. Allg. Chem. 1977, 435, 146-152.

ISBN:978-0-471-19957-1; pp. 702-703, Tables 17-B-1, 17-C-1, 17-D-1, 17-E-1, 18-C-1.

Beilin, SI et al., 'A new method for the synthesis of organometallic . . . in their lowest oxidation states', Journal of Organometallic Chemistry, 1977, 142, 145-148.

Barker, GK et al., Silylmethyl and Related Complexes. Part 6. Preparation. Properties, and Crystal and Molecular Structure of Tris[bis(trimethylsilyl) methyl]-chromium(III); . . . JCS Dalton, 1978, 734-740.

Smith, PD et al., 'Ethylene Polymerization Catalysts from . . . Chromium Alkyls', Journal of Polymer Science: Part A: Polymer Chemistry, 1990, 28, 3587-3601.

Vitillo, et al.; "Role of Exposed Metal Sites in Htdrogen Storage in MOFs" J. Am. Chem. So. 2008; 130; 8686-8696.

\* cited by examiner

Figure 5: Powder X-ray diffraction of vanadium hydrazide materials. From top to bottom: A150, B150, C150, and D150 samples.

Figure 6: Nitrogen adsorption – desorption isotherms. Samples were measured on an ASAP-2010 instrument at 77K.

Figure 7: Valence region of XPS spectrum of vanadium hydrazide materials heated to 150 °C with different ratios of hydrazine.

Figure 8: Vanadium 2p1/2 and 2p3/2 and oxygen 1S region of XPS spectrum of vanadium hydrazide materials heated to 150 °C with different ratios of hydrazine.

Figure 9: Peak fitting of vanadium 2p1/2 and 2p3/2 emissions in the XPS spectrum of A150 sample.

Figure 10: Peak fitting of vanadium 2p1/2 and 2p3/2 emissions in the XPS spectrum of B150 sample.

Figure 11: Peak fitting of vanadium 2p1/2 and 2p3/2 emissions in the XPS spectrum of C150 sample.

Figure 12: Peak fitting of vanadium 2p1/2 and 2p3/2 emissions in the XPS spectrum of D150 sample.

Figure 13: N 1S region of XPS Spectrum of vanadium hydrazide materials heated to 150 °C with different ratios of hydrazine.

Figure 14: Peak fitting of N 1S region of XPS Spectrum of A150 sample.

Figure 15: Peak fitting of N 1S region of XPS Spectrum of B150 sample.

Figure 16: Peak fitting of N 1S region of XPS Spectrum of C150 sample.

Figure 17: Peak fitting of N 1S region of XPS Spectrum of D150 sample.

Figure 18: Hydrogen adsorption – desorption excess storage isotherms of A-series vanadium hydrazide materials synthesized with a V:hydrazine ratio of 4:3. Desorption isotherms recorded at 298 K omitted for clarity.

Figure 19: Hydrogen adsorption – desorption excess storage isotherms of B-series vanadium hydrazide materials synthesized with a V:hydrazine ratio of 1:1. Desorption isotherms recorded at 298 K omitted for clarity.

Figure 20: Hydrogen adsorption – desorption excess storage isotherms of C-series vanadium hydrazide materials synthesized with a V:hydrazine ratio of 1:1.5. Desorption isotherms recorded at 298 K ommitted for clarity.

Figure 21: Hydrogen adsorption – desorption excess storage isotherms of D-series vanadium hydrazide materials synthesized with a V:hydrazine ratio of 1:2. Desorption isotherms recorded at 298 K omitted for clarity.

Figure 22: Hydrogen adsorption capacity at 298K in a 20 cycle test of the C150 sample.

Figure 23: Heat of hydrogen adsorption on vanadium hydrazide materials and carbon AX-21.

Figure 24: Room-temperature EPR spectra of vanadium hydrazide gel C150, (a) prior to exposure to hydrogen gas, and (b) after exposure to hydrogen gas. Insets: low-field region magnified by a factor of ten. *Experimental conditions:* frequency = 9.382 GHz, microwave power = 20 mW, time constant = 20.48 ms, modulation amplitude = 10 G, average of three 45 s scans.

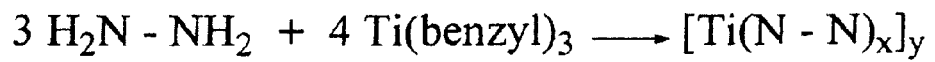
$$3\ H_2N\text{-}NH_2 + 4\ Ti(benzyl)_3 \longrightarrow [Ti(N\text{-}N)_x]_y$$
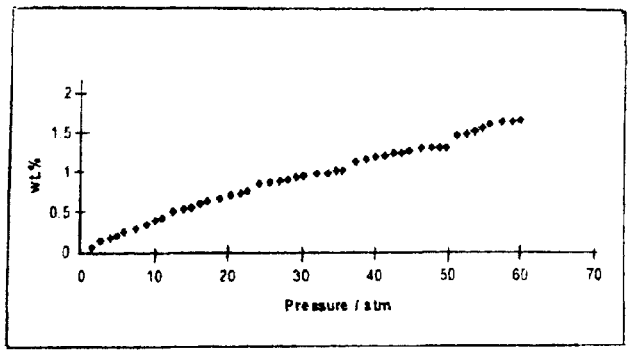
Dried at 100°C
density=1.03
Figure 26(a)
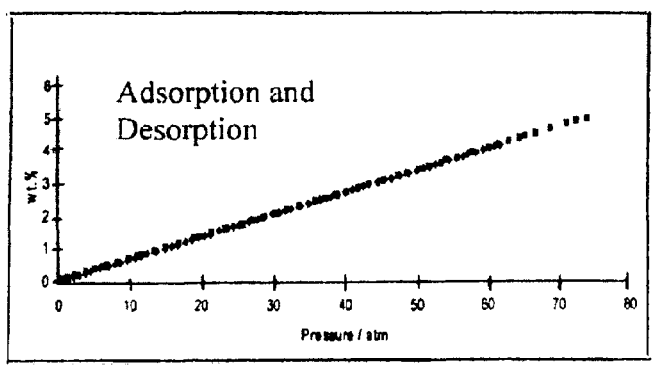
Dried at 150°C
density=2.44
Figure 26(b)

tris [bis(trimethylsilyl)methyl]Titanium

METAL HYDRAZIDE MATERIALS

RELATED APPLICATIONS

This application claims the benefit of 35 U.S.C. §119(e) to U.S. Provisional Application No. 61/193,780 filed Dec. 23, 2008.

SCOPE OF THE INVENTION

The present invention relates to metal hydrazide materials, and in particular, to metal hydrazide polymers useful for storing hydrogen.

BACKGROUND OF THE INVENTION

Hydrogen is a well known alternative energy source that has more than three times the energy density by mass than currently used hydrocarbon fuels, such as gasoline. However, hydrogen has the disadvantage of being difficult to store and transport. Using current technology, hydrogen storage has a low energy storage density by volume relative to hydrocarbon fuels. Therefore, with all other factors beings equal, in order to store the same amount of energy, hydrogen storage requires a much larger and heavier storage tank than hydrocarbon fuel storage.

Gravimetric capacity is a measure of the amount of hydrogen that can be stored per unit mass of the storage system. Volumetric capacity is a measure of the amount hydrogen that can be stored per unit volume of the storage system. The United States Department of Energy (DOE) has set targets for hydrogen storage for 2010 and 2015. By 2010, the DOE target is to store hydrogen at a gravimetric capacity of about 6 wt % and a volumetric capacity of about 60 kg/m$^3$. By 2015, the DOE target is to store hydrogen at a gravimetric capacity of about 9 wt % and a volumetric capacity of about 80 kg/m$^3$.

Compression techniques have been used to increase gas pressure and improve the energy storage density by volume for hydrogen. This allows for the storage tanks to be smaller. However, the compressing of hydrogen requires a significant amount of energy, often accounting for as much as 30% of the stored energy. Furthermore, large pressure vessels are required for such compression techniques.

Another technique for storing hydrogen involves converting hydrogen gas to liquid hydrogen. This technique requires cryogenic storage because hydrogen has a very low boiling point of −252.882° C. or −423.188° F. The liquification of hydrogen requires a large amount of energy to maintain these extremely low temperatures. Furthermore, the storage tank for liquid hydrogen requires complex and expensive insulation in order to prevent the liquid hydrogen from boiling off. In addition, liquid hydrogen has a lower energy density by volume than hydrocarbon fuels, such as gasoline, by a factor of about 4.

A further technique of hydrogen storage involves reacting $H_2$ with another compound. Metal hydrides, such as LiH and $NaAlH_4$, are commonly used in this technique. However, hydrides have the disadvantage of being generally combustible upon exposure to moist air, and are toxic to humans.

When hydrogen is reacted with the metal hydride, significant amounts of heat are given off. When this heat is given off, a step of cooling must be carried out to prevent a significant rise in temperature in the system, and this cooling step constitutes an energy loss to the system.

An automobile or truck can have a storage tank containing metal hydrides to be reacted with hydrogen. However, filling this storage tank with hydrogen is a slow process, often requiring more than 3 minutes. Also, storing hydrogen using metal hydrides requires a larger and heavier storage tank relative to the storage tanks used for storing hydrocarbon fuels.

In order to release the hydrogen from the metal hydride, heating of the metal hydrides to temperatures as high as 250° C. is required. This heating step results in a significant loss of energy.

SUMMARY OF THE INVENTION

The present invention provides novel polymers. In one aspect, the present invention provides a polymer comprising -[$MN_2$]— as a repeating unit, wherein M is selected from the group consisting of Sc, Ti, V, Cr, Mn, Fe, Co, Zr, Nb, Mo, and mixtures thereof. In another aspect, the present invention provides a polymer comprising -[$M_2N_3$]— as a repeating unit, wherein M is selected from the group consisting of Sc, Ti, V, Cr, Mn, Fe, Co, Zr, Nb, Mo, and mixtures thereof.

In another aspect, the present invention provides a polymer comprising a repeating unit selected from the group consisting of -[$MN_2$]—, -[$M_2N_3$]—, and mixtures thereof, wherein M is selected from the group consisting of Sc, Ti, V, Cr, Mn, Fe, Co, Zr, Nb, Mo, and mixtures thereof.

To at least partially overcome the disadvantages of previously known hydrogen storage techniques, the present invention provides new polymers and compounds for use in hydrogen storage, methods of producing such polymers and compounds, methods of using such polymers and compounds for storing hydrogen, and systems for storing hydrogen using such polymers and compounds.

An object of the present invention is to provide new materials for use in hydrogen storage.

Another object of the present invention is to provide materials which can store and release hydrogen without requiring the input of a significant amount of energy during the binding or release of hydrogen.

M is preferably a transition metal, and more preferably an early transition metal. Preferably, M is selected from the group consisting of Ti, V, Cr, and mixtures thereof. More preferably, M is Ti or V.

The polymers of the present invention are preferably in gel form or solid form. Preferably, the polymers of the present invention are in crystalline form.

The polymers of the present invention may contain one or more residual groups in the structure of the polymer. Preferably, the one or more residual groups are present in an amount of 40% by weight of the polymer or less, more preferably 25% by weight of the polymer or less, and more preferably 10% by weight of the polymer or less. Preferably, the one or more residual groups comprise one or more atoms selected from the group consisting of C, N and H.

The polymers of the present invention are preferably used for hydrogen storage. The polymers of the present invention are able to bind and store hydrogen without requiring any significant input of heat energy to facilitate the binding. At a room temperature of 20° C. to 25° C. and at a pressure of 75 to 90 atm, the polymers of the present invention, where M is Ti, can preferably store hydrogen at a gravimetric capacity of 4 to 9 wt % and at a volumetric capacity of 80 to 180 kg/m$^3$, and more preferably at a gravimetric capacity of 6 wt % and at a volumetric capacity of 150 kg/m$^3$.

In another aspect, the present invention provides a method of storing hydrogen in a system, said method comprising: (i) providing a polymer in the system, wherein the polymer comprises repeating units selected from the group consisting of -[$MN_2$]—, -[$M_2N_3$]—, and mixtures thereof, wherein M is selected from the group consisting Sc, Ti, V, Cr, Mn, Fe, Co, Zr, Nb, Mo, and mixtures thereof; (ii) adding hydrogen to the system; and (iii) allowing the hydrogen to bind with the polymer.

Preferably, the hydrogen binds with the M atoms in the polymer. Preferably, the hydrogen binds to M by the Kubas interaction.

Preferably, the polymer in the system is in gel form. Preferably, when the hydrogen binds to the polymer, the hydrogen becomes a component of the gel.

The method of storing hydrogen in a system of the present invention is preferably carried out without adding heat to the system. Preferably, the method of storing hydrogen in a system of the present invention is carried out without cooling the system.

The system preferably has a temperature of up to 200° C., more preferably −300° C. to 150° C., more preferably −200° C. to 100° C., more preferably 0° C. to 50° C., more preferably 10° C. to 30° C., and even more preferably 20° C. to 25° C. The system is preferably free of oxygen to prevent the oxidation of metal in the polymer.

In the method of storing hydrogen of the present invention, the step of adding hydrogen to the system increases hydrogen pressure in the system. This increase in hydrogen pressure allows the polymer in the system to bind and store greater amounts of hydrogen. Preferably, the hydrogen pressure in the system is increased to 30 atm or more, more preferably 30 atm to 500 atm, even more preferably 50 atm to 200 atm, and even more preferably 75 atm to 100 atm.

The method of storing hydrogen of the present invention preferably further comprises a step of releasing the hydrogen pressure in the system. Releasing the hydrogen pressure in the system causes the hydrogen to be released from the polymer. The step of releasing the hydrogen pressure in the system is preferably carried out by allowing hydrogen gas to escape from the system, thus decreasing the hydrogen pressure. Preferably, the step of releasing the hydrogen pressure decreases the hydrogen pressure in the system to 100 atm or less, more preferably 50 atm or less, more preferably 30 atm or less, and even more preferably 20 atm or less.

There is a linear relationship between the hydrogen pressure in the system and the volumetric capacity of the polymers in the system. Specifically, as the hydrogen pressure is increased in the system, the polymers of the present invention are able to store greater amounts of hydrogen. When the system is being filled with hydrogen, the hydrogen pressure in the system is preferably increased, thus allowing more hydrogen to be stored. The hydrogen pressure in the system is preferably increased using a compressor, preferably a gas compressor, which pumps hydrogen into the system.

When desired, the hydrogen can be released from the polymers of the present invention by decreasing the hydrogen pressure in the system. A step of decreasing the pressure in the system can be conducted at room temperature. Furthermore, no heat energy needs to be added to the system in order to release the hydrogen from the polymers of the present invention. Preferably, the hydrogen pressure is decreased when hydrogen gas is allowed to escape from the system. At room temperature, virtually 100% of the hydrogen that is added into the system can be released from the system when desired.

In another aspect, the present invention provides a system for storing hydrogen, the system comprising a storage tank and a polymer inside the storage tank, wherein the polymer comprises repeating units selected from the group consisting of -[$MN_2$]—, -[$M_2N_3$]—, and mixtures thereof, wherein M is selected from the group consisting Sc, Ti, V, Cr, Mn, Fe, Co, Zr, Nb, Mo, and mixtures thereof.

Preferably, the storage tank comprises one or more openings in a wall of the storage tank. Fluids, such as hydrogen gas, can preferably pass into and out of the storage tank through the one or more openings. The system for storing hydrogen preferably further comprises one or more valves which control the passage of fluids through the one or more openings. The one or more valves can preferably be used to release pressure inside the storage tank by opening said one or more valves and allowing fluids to pass out of the storage tank through the one or more openings. Preferably, the system further comprises a compressor for adding hydrogen into the storage tank. Preferably, the compressor is a gas compressor which pumps hydrogen into the storage tank, thus increasing hydrogen pressure inside the storage tank.

The storage tank is preferably enclosed. Preferably, the storage tank is made of metal, and more preferably, the storage tank is made of steel or aluminum. Alternatively, the storage tank may be made of a composite material, such as a composite of fibreglass and aramid. Alternatively, the storage tank may be made of a carbon fibre with a liner. The liner may be a polymer liner, such as a thermoplastic liner, or a metal liner, such as a steel liner or an aluminum liner.

Hydrogen may be added and stored in the system, and subsequently released from the system, many times without a significant decrease in the hydrogen storage capacity of the system. A significant decrease in the hydrogen storage capacity of the system would be, for example, a decrease of 10% by weight of the total hydrogen that the system can store. Preferably, the system can be filled with hydrogen and subsequently release hydrogen at least 1000 times without a significant decrease in the storage capacity of the system, more preferably at least 1500 times, and even more preferably at least 2000 times.

The present invention also provides novel methods for producing the novel polymers of the present invention. A preferred method comprises: (i) reacting M with R to produce compounds selected from the group consisting of $MR_3$, $MR_4$, and mixtures thereof, wherein M is selected from the group consisting Sc, Ti, V, Cr, Mn, Fe, Co, Zr, Nb, Mo, and mixtures thereof, and R is a sterically demanding group or a group that protects a low coordination number for M; and (ii) reacting the compounds selected from the group consisting of $MR_3$, $MR_4$, and mixtures thereof with hydrazine to produce a polymer comprising repeating units selected from the group consisting of -[$MN_2$]—, -[$M_2N_3$]—, and mixtures thereof.

Preferably, the step of reacting the compounds selected from the group consisting of $MR_3$, $MR_4$, and mixtures thereof with hydrazine is carried out in an inert atmosphere. The inert atmosphere may, for example, comprise nitrogen. Preferably, the inert atmosphere is free of oxygen.

Preferably, the step of reacting the compounds selected from the group consisting of $MR_3$, $MR_4$, and mixtures thereof with hydrazine is carried out in the presence of a solvent. The solvent is preferably a hydrocarbon solvent, such as, but not limited to benzene, kerosene, toluene and xylene.

In either the presence or the absence of a solvent, heat energy may be input during the step of reacting the compounds selected from the group consisting of $MR_3$, $MR_4$, and mixtures thereof with hydrazine to increase the rate of the reaction.

Preferably, the step of reacting the compounds selected from the group consisting of $MR_3$, $MR_4$, and mixtures thereof with hydrazine is carried out at a temperature of 0° C. to 300° C., more preferably 50° C. to 200° C., and even more preferably 100° C. to 200° C.

Preferably, the step of reacting the compounds selected from the group consisting of $MR_3$, $MR_4$, and mixtures thereof with hydrazine is carried out at a pressure of 1 atm to 10 atm, more preferably 1 atm to 4 atm, and even more preferably 1 atm to 2 atm. Contamination of the reaction is reduced when the pressure is raised above 1 atm.

In another aspect, the present invention provides a method of producing a polymer, said method comprising: (i) reacting Cr with $(CH_3)_3SiCH_2$ to produce $Cr_4[(CH_3)_3SiCH_2]_8$; and (ii) reacting $Cr_4[(CH_3)_3SiCH_2]_8$ with hydrazine to produce a polymer, wherein the polymer comprises repeating units selected from the group consisting of —[$CrN_2$]—, —[$Cr_2N_3$]—, and mixtures thereof. In this method, the novel intermediate compound is $Cr_4[(CH_3)_3SiCH_2]_8$.

The present invention also provides novel compounds which act as intermediates in the method of producing the polymers of the present invention. In one aspect, the present invention provides a compound having the chemical formula $MR_3$, wherein M is selected from the group consisting of Sc, Ti, V, Cr, Mn, Fe, Co, Zr, Nb, Mo, and mixtures thereof, and R is a sterically demanding group or a group that protects a low coordination number for M. In another aspect, the present invention provides a compound having the chemical formula $MR_4$, wherein M is selected from the group consisting of Sc, Ti, V, Cr, Mn, Fe, Co, Zr, Nb, Mo, and mixtures thereof, and R is a sterically demanding group or a group that protects a low coordination number for M.

Preferably, M is selected from the group consisting of Ti, V, Cr, and mixtures thereof. More preferably, M is Ti or V.

R can preferably be a sterically demanding group selected from the group consisting of an alkyl group, an alkenyl group, an alkynyl group, and an amido group. These sterically demanding groups may be substituted or unsubstituted. A substituent may replace a hydrogen atom in any of the alkyl group, alkenyl group, alkynyl group or amido group. These sterically demanding groups may be straight chain or branched or cyclic or the like.

The alkyl group preferably comprises 1 to 8 carbon atoms, more preferably 1 to 4 carbon atoms, and even more preferably is methyl.

R can preferably be a group that protects a low coordination number for M selected from the group consisting of an aryl group, an ether group, and an alkenyl group.

The aryl group may be substituted or unsubstituted. A substituent may replace a hydrogen atom in the aryl group. The aryl group can preferably be selected from the group consisting of a phenyl group, a benzyl group, a tolyl group, a xylyl group, and a naphthyl group, and is more preferably a benzyl group. A preferred benzyl group is a mesityl group, which is also known as a 1,3,5-trimethylbenzyl group.

The ether group may be substituted or unsubstituted. A substituent may replace a hydrogen atom in the ether group. The ether group is preferably tetrahydrofuran. The ether group may be straight chain or branched or cyclic or the like.

The alkenyl group may be substituted or unsubstituted. A substituent may replace a hydrogen atom in the alkenyl group. The alkenyl group is preferably an allyl group. The alkenyl group may be straight chain or branched or cyclic or the like.

A preferred example of R is bis(trimethylsilyl)methyl. Another preferred example of R is pentylene.

Preferred examples of the novel intermediate compound include, but are not limited to, trismesitylvanadium, tribenzyltitanium, tris[bis(trimethylsilyl)methyl]titanium, and trispentylenetitanium. Other preferred examples of the novel intermediate compound include, but are not limited to, $V(mesityl)_3$.tetrahydrofuran and tetrabenzyltitanium.

The coordination number for M is the number of points at which ligands are attached to M, where the ligands are attached to M either by single bonds or multiple bonds. A group that is "sterically demanding" is a group that binds to M, and due to the sterically demanding group's size, prevents other ligands from binding with M. Examples of such sterically demanding groups are alkyl groups, alkenyl groups, alkynyl groups and amido groups. Preventing other ligands from binding with M maintains a low coordination number for M.

A group that "protects a low coordination number for M" is a group that binds to M, and prevents other ligands from binding with M. Examples of such groups are aryl groups and alkenyl groups. Preventing other ligands from binding with M maintains a low coordination number for M. The group can prevent other ligands from binding to M by means known to persons skilled in the art, such as by steric effects and/or electronic effects. Steric effects may include, but are not limited to, steric hindrance and steric shielding. Electronic effects may include, but are not limited to, induction, conjunction, orbital symmetry, electrostatic interactions and spin state.

The polymers of the present invention are useful in other applications, such as propellants, battery technologies, sorbents, and sensors.

A propellant is a material that is used to move or propel an object, such as a jet or rocket. A propellant may comprise a fuel and an oxidizer. The fuel may be, for example, gasoline, jet fuel or rocket fuel.

The polymers of the present invention may preferably be used in a propellant. Preferably, the propellant further comprises $H_2$, and the $H_2$ binds to M of the polymers of the present invention. The binding of $H_2$ preferably binds to M by a Kubas interaction. The $H_2$ is preferably in liquid form.

Preferably, the propellant further comprises an oxidizer. Preferably, the oxidizer is liquid oxygen.

Preferably, the propellant is used to propel a jet or a rocket.

A battery comprises one or more electrochemical cells which convert stored chemical energy into electrical energy. The polymer of the present invention may preferably be used to bind to and store a compound in a battery. The compound that is stored may preferably be $H_2$. Preferably, the battery converts energy stored in the $H_2$ into electrical energy.

A sorbent is a material that is used to absorb a liquid or a gas. The polymer of the present invention may preferably be used as a sorbent to absorb a liquid or a gas. Preferably, the polymer of the present invention absorbs hydrogen. The hydrogen is preferably in liquid form or in gas form.

A sensor is used to detect a substance or to measure a physical quantity. The sensor gives a signal that the substance has been detected or gives a signal representing the measurement of the physical quantity. The signal can be read by an observer or by an instrument.

The polymer of the present invention may preferably be used in a sensor. Preferably, the polymer of the present invention detects hydrogen in a system. Preferably, the polymer of the present invention measures the amount of hydrogen that is present in a system. The hydrogen is preferably in liquid form or in gas form.

In another aspect, the present invention provides use of the polymer of the present invention for hydrogen storage.

BRIEF DESCRIPTION OF THE DRAWINGS

Further aspects and advantages will become apparent from the following description taken together with the accompanying drawings in which:

FIG. 26 shows the hydrogen adsorption-desorption isotherms of two preferred titanium hydrazide materials which are: (a) dried at 100° C.; and (b) dried at 150° C.

Throughout all the drawings and the disclosure, similar parts are indicated by the same reference numerals.

DESCRIPTION OF PREFERRED EMBODIMENTS

Reference is made to FIGS. 1 to 4, which show preferred embodiments of the present invention.

A preferred method for producing a preferred embodiment of the polymers according to the present invention is set out below.

The preferred starting material is a transition metal. A transition metal is understood as referring to an element whose atom has an incomplete d sub-shell, or which can give rise to cations with an incomplete d sub-shell. The atoms of transition metals can have between 1 to 10 d electrons in the outermost shell. The presence of d electrons in the outermost shell make transition metals suitable for Kubas interactions, as described below. The preferred transition metals for use in the present invention are early transition metals, preferably with low valency numbers and low coordination numbers.

Ti is used as a starting material in the preferred method described herein. In other preferred methods, Sc, V, Cr, Mn, Fe, Co, Zr, Nb, Mo, or mixtures thereof can be used.

The starting material, Ti, is reacted with R groups. The R groups are preferably sterically demanding groups, such as, but not limited to, alkyl groups, alkenyl groups, alkynyl groups, and amido groups. The R groups may also preferably be groups that protect a low coordination number for Ti, such as, but not limited to, aryl groups, ether groups, and alkenyl groups. The R groups may be substituted or unsubstituted. The R groups may be straight chain or branched or cyclic or the like.

In the preferred method, the R groups are alkyl groups. The alkyl groups may be, for example, methyl, ethyl, propyl, butyl or pentyl. The alkyl groups may be straight chain or branched or cyclic or the like. In the preferred method described herein, the alkyl groups are methyl groups.

The reaction of Ti with methyl groups preferably produces the following novel intermediate compounds:

(i) $MR_3$, wherein M is Ti and R is methyl; and
(ii) $MR_4$, wherein M is Ti and R is methyl.

Figure 1:
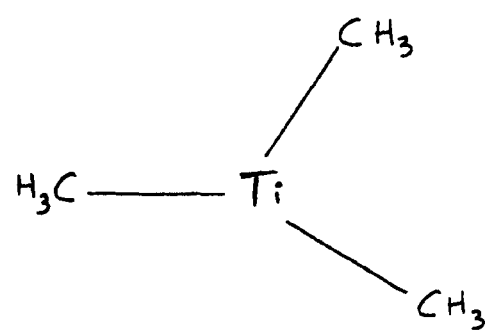
FIG. 1 illustrates a preferred embodiment of the novel intermediate compounds of the present invention.

FIG. 1 illustrates a preferred embodiment of the novel intermediate compounds of the present invention. Specifically, FIG. 1 illustrates a preferred embodiment of $MR_3$, wherein M is Ti, and R is the alkyl group $CH_3$.

In the preferred method, the intermediate compounds, $MR_3$ and $MR_4$, are then reacted with hydrazine, $N_2H_4$. This reaction preferably takes place in an inert atmosphere. The inert atmosphere preferably comprises nitrogen. Preferably, the inert atmosphere is free of oxygen to prevent oxidation of M.

The reaction of the intermediate compounds with hydrazine preferably takes place in the presence of a solvent, more preferably a hydrocarbon solvent. Preferred hydrocarbon solvents may be, but are not limited to, benzene, kerosene, toluene, and xylene.

The reaction of the intermediate compounds with hydrazine preferably takes place at a temperature of 0° C. to 300° C., more preferably at a temperature of 50° C. to 200° C., and even more preferably at a temperature of 100° C. to 200° C. Preferably, heat energy is added to increase the rate of the reaction.

In the preferred method, the reaction of the intermediate compounds, $MR_3$ and $MR_4$, with hydrazine produces preferred polymers of the present invention, wherein said polymers have the following repeating units:

(i) -[$MN_2$]— wherein M is Ti; and
(ii) -[$M_2N_3$]— wherein M is Ti.

Figure 2:
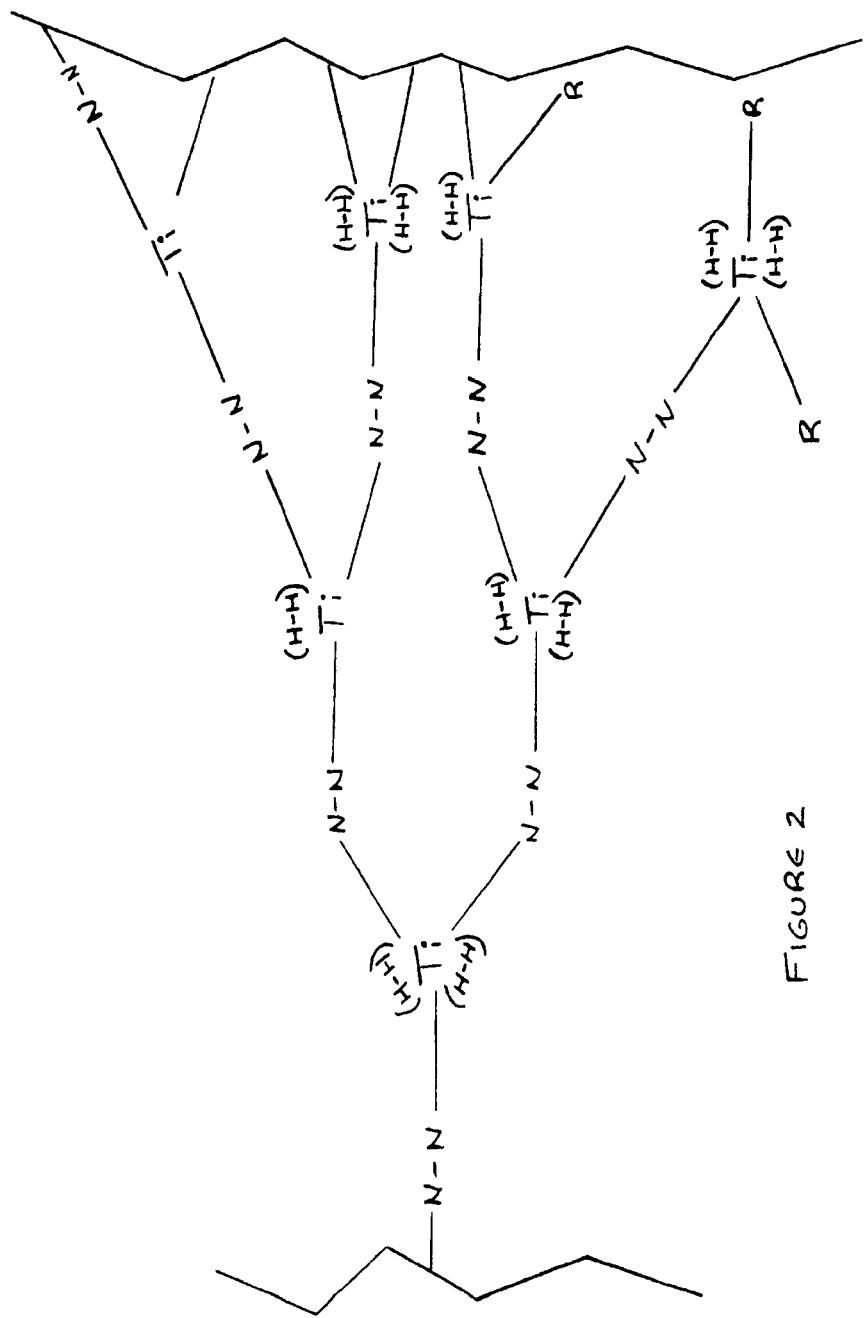
FIG. 2 illustrates a preferred embodiment of the novel polymers of the present invention with $H_2$ bound to the metal centres of the polymer.

FIG. 2 illustrates a preferred embodiment of the novel polymers of the present invention, where the preferred embodiment has the repeating unit -[$MN_2$]—, wherein M is Ti. FIG. 2 also shows residual R groups within the structure of the polymer.

The polymers of the present invention are referred to in the present application as "metal hydrazide polymers". In the present application, the term "metal hydrazide" refers to the reaction of the metal, M, with hydrazine, $N_2H_4$, to form the polymers of the present invention.

The polymers of the present invention may be amorphous three-dimensional polymers with no long range order in the position of the atoms in the polymer structure. The polymers may be in the form of a gel or a solid. These polymers may also be in crystalline form with a more ordered structure than the gel form.

The metal hydrazide polymers of the present invention may have residual R groups or residual NH groups present within the structure of the polymers. The residual R groups are derived from the intermediate compounds $MR_3$ and $MR_4$ where, during the reaction of $MR_3$ and $MR_4$ with hydrazine, not all of the R groups of $MR_3$ and $MR_4$ were replaced with N. The residual NH groups are derived from hydrazine where, during the reaction of $MR_3$ and $MR_4$ with hydrazine, not all of the H groups of hydrazine were replaced with M.

The metal hydrazide polymers of the present invention preferably have a surface area of less than 50 $m^2/g$, and are preferably microporous with pores having a diameter less than 10 Å.

The metal hydrazide polymers of the present invention may be preferably be used for storing hydrogen. A preferred system of hydrogen storage can include a pressure vessel. The pressure vessel preferably holds the metal hydrazide polymers of the present invention at a temperature of up to 200° C., more preferably −300° C. to 150° C., more preferably −200° C. to 100° C., more preferably 0° C. to 50° C., more preferably 10° C. to 30° C., and more preferably 20° C. to 25° C. Preferably, in order to prevent oxidation of the metal, M, there is no oxygen inside the pressure vessel. Hydrogen is added into the pressure vessel and stored using the metal hydrazide polymers of the present invention. No heating is required when adding hydrogen to the pressure vessel for storage.

The metal hydrazide polymers of the present invention may preferably store hydrogen by the Kubas interaction. In the Kubas interaction, $H_2$ binds in a non-dissociative manner to a metal centre, M. The $H_2$ binds to the metal centre where the metal center has a low coordination number, such as three or four.

The amount of hydrogen that can be stored by the polymers of the present invention is proportional to the pressure in the pressure vessel. At higher pressures, more hydrogen can be stored by the polymers of the present invention.

The pressure in the pressure vessel is preferably increased by adding hydrogen into the pressure vessel. As the pressure is increased, the number of Kubas interactions per metal center increases. When M is Ti in the polymer, and there is a pressure of 75 to 90 atm in the pressure vessel, there are preferably two Kubas interactions per metal Ti center of the polymer. When M is Ti in the polymer, the theoretical storage limit is five Kubas interactions per metal centre. Therefore, increasing the pressure in the system could increase the number of Kubas interactions per metal center to five or more, thus allowing a greater amount of hydrogen to be stored.

FIG. 2 illustrates a preferred embodiment of the polymer of the present invention, where $H_2$ is bound to the metal centres, Ti, of the polymer. Specifically, FIG. 2 illustrates a polymer having the repeating unit -[$MN_2$]—, wherein M is Ti. As shown in FIG. 2, hydrogen is stored by the polymer where the (H—H) binds to the metal Ti centres of the polymer. In the preferred embodiment shown in FIG. 2, up to two (H—H) can be bound to each metal Ti centre. However, more (H—H) can be bound per metal centre. For example, five (H—H) can be bound to a metal center in the polymer of the present invention.

In one experiment, it has been found that, at a room temperature of 20° C. to 25° C. and at a pressure of 75 to 90 atm, the polymers of the present invention, where M is Ti, are able to store hydrogen at a gravimetric capacity of about 6 wt % and at a volumetric capacity of about 150 $kg/m^3$.

The large amounts of hydrogen capable of being stored by the metal hydrazide polymers of the present invention is due to the fact that the metal centres of the polymers have low coordination numbers, such as three or four. A low coordination number means the metal center has a low number of points at which ligands are attached to the metal centre, such as three or four. A metal center with a low number of points to which ligands are attached has free d-electrons. In the Kubas interaction, the free d-electrons of the metal center interact with hydrogen. Specifically, in the Kubas interaction, where the metal center has a low coordination number, the $H_2$ shares one of its two electrons with the metal centre, and the metal back donates electrons by overlap of its d-orbital with an empty orbital of $H_2$.

When a metal center has a high coordination number, such as six, little or no hydrogen can be stored. The metal centres have six ligands bonded to them, and this does not leave enough free d-electrons to interact with hydrogen. In contrast, the metal hydrazide polymers of the present invention have metal centres with a low coordination number of only three or four. Therefore, the metal centres have free d-electrons to interact with hydrogen by the Kubas interaction.

In the method of producing the polymers of the present invention, hydrazine is preferably used to react with the intermediate compounds, $MR_3$ and $MR_4$, to produce the polymers of the present invention having the repeating units -[$MN_2$]— and -[$M_2N_3$]—. In the polymers of the present invention, there is a two atom linker, specifically —N—N—, between metal centres. It has been found that this polymer structure provides metal centres with low coordination numbers, and such metal centres can bind $H_2$. The two atom linker is large enough so as to keep the metal centres apart and prevent them from clustering. At the same time, the two atom linker is small enough to minimize void space which can reduce the volumetric capacity of the polymer.

If $NH_3$ or $H_2O$ are used instead of hydrazine to react with the intermediate compounds, $MR_3$ and $MR_4$, this produces polymers where there are one atom linkers, —N— or —O—, between metal centres. In these polymers, the metal centres have a coordination number of six. As such, these polymers are not able to store hydrogen.

If hydrogen peroxide is used instead of hydrazine to react with the intermediate compounds, $MR_3$ and $MR_4$, this produces polymers where there are two atom linkers, specifically —O—O—, between metal centres. However, hydrogen peroxide oxidizes the metal centre. It has been found that such metal centres with a high oxidation state cannot bind hydrogen.

If $CH_2$—$CH_2$ is used instead of hydrazine to react with the intermediate compounds, $MR_3$ and $MR_4$, this produces polymers where there are two atom linkers, specifically —C—C—, between metal centres. However, when hydrogen is added to the system, the M-C bond is readily cleaved by $H_2$. Therefore, these polymers are not stable in the presence of hydrogen.

Polymers with larger linkers, such as three atom linkers and four atom linkers, between metal centres are disadvantageous because they are heavier, thus reducing gravimetric capacity. Furthermore, polymers with larger linkers tend to chelate, where a single ligand forms two or more separate bonds with a single metal centre. This chelated structure leads to the formation of molecular monomers rather than extended polymer structures.

In order to release the hydrogen from the polymers of the present invention, the pressure in the pressure vessel is decreased. No heating is required to release the hydrogen from the polymers. Preferably, a valve is opened to allow hydrogen gas to escape from the pressure vessel, thus decreasing the pressure in the pressure vessel. When the pressure is decreased, virtually 100% of the stored hydrogen is released.

Hydrogen may be added or released from the system at any point throughout the entire pressure gradient of the system without any adverse effects to the storage capacity of the system. Hydrogen may be added or released from the system any number of times without any adverse effects to the storage capacity of the system. Preferably, the system can be filled with hydrogen and emptied of hydrogen at least 1500 times without any adverse effects to the storage capacity of the system.

When the pressure vessel is used as a fuel tank for a land vehicle, such as an automobile or truck, the fuel tank can be filled with hydrogen in a short time, preferably 3 minutes or less, and more preferably 2 minutes or less. A fuel tank filled with hydrogen preferably stores enough energy to allow the land vehicle to travel a long distance without the need to refill, preferably 200 miles or more, more preferably 300 miles or more, and even more preferably 400 miles or more.

Figure 3:
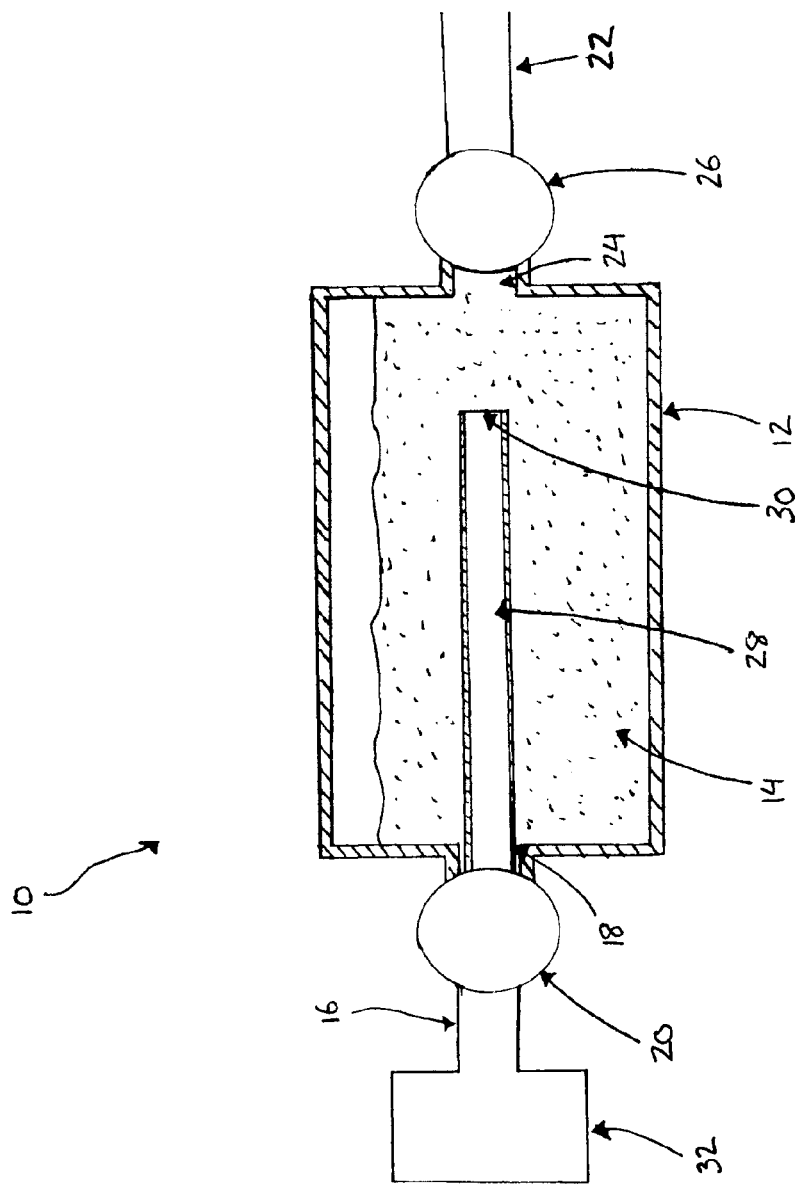
FIG. 3 illustrates a cross-sectional view of a preferred embodiment of the system for storing hydrogen of the present invention.
Figure 4:
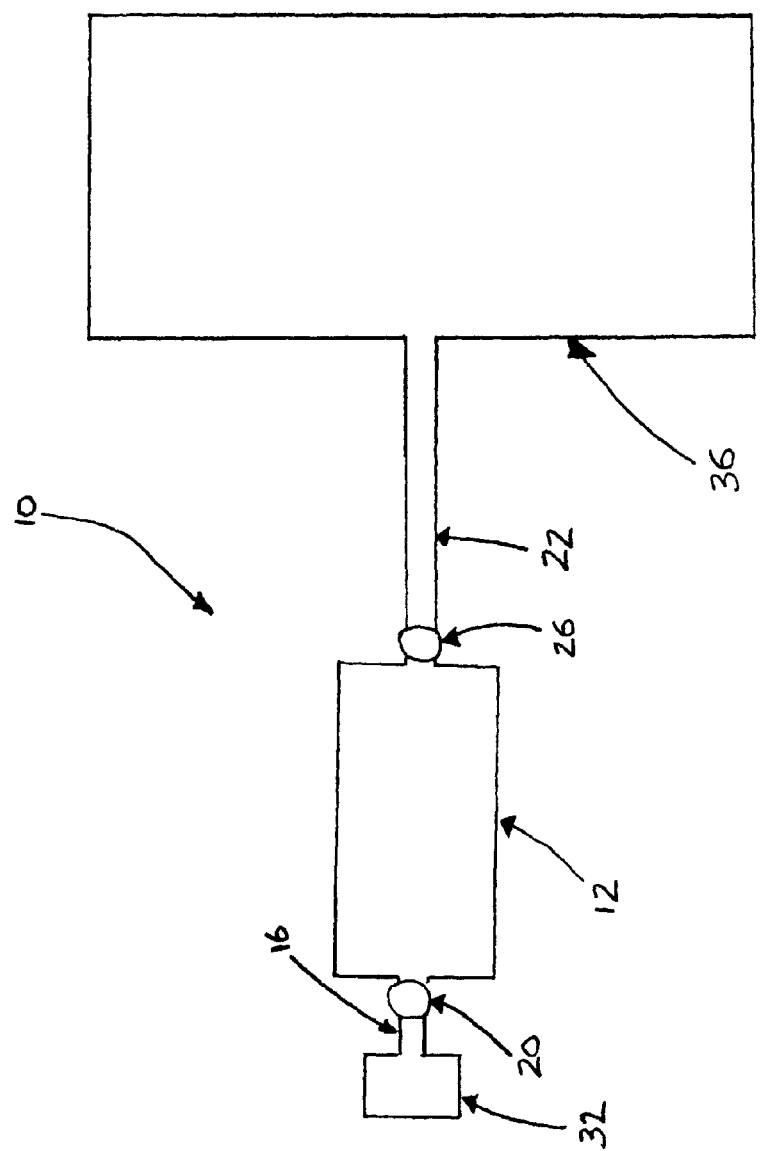
FIG. 4 illustrates the preferred embodiment of the system shown in FIG. 3 attached to a hydrogen fuel cell.

FIGS. 3 and 4 illustrate a preferred embodiment of the system for storing hydrogen of the present invention. The preferred system 10 can be used, for example, in a land vehicle such as an automobile or truck.

The system 10 comprises a tank body 12 which is made of a material that is impermeable to hydrogen gas, thus preventing undesired leaking of the hydrogen gas out of the tank body 12. Preferably, the tank body 12 is made of metal, and more preferably, the tank body 12 is made of steel or aluminum. Alternatively, the tank body 12 may be made of a composite material, such as a composite of fibreglass and aramid. Alternatively, the tank body 12 may be made of a carbon fibre with a liner. The liner may be a polymer liner, such as a thermoplastic liner, or a metal liner, such as a steel liner or an aluminum liner.

The polymer 14 of the present invention is present inside the tank body 12. In FIG. 3, the polymer 14 is in a gel form. The polymer 4 may partially fill or totally fill the tank body 12.

A first passage 16 leads to a first opening 18 in the wall of the tank body 12. A first valve 20 controls the flow of hydrogen gas through the first opening 18.

A second passage 22 extends from a second opening 24 in the wall of the tank body 12. A second valve 26 controls the flow of hydrogen gas through the second opening 24.

The first valve 20 and the second valve 26 can be any type of valves that control the flow of hydrogen gas through the first opening 18 and the second opening 24, respectively. For example, the first valve 20 and the second valve 26 can be ball valves or a gate valves.

Hydrogen is preferably added to the system 10 as follows. A gas compressor 32 pumps hydrogen gas into the first passage 16. The first valve 20 is opened to allow the hydrogen gas to flow through the first opening 18 and into the tank body 12.

A passage tube 28 is in gaseous communication with the first opening 18 and extends into the interior of the tank body 12. The passage tube 28 facilitates the distribution of the hydrogen gas to the polymer 14. The passage tube 28 is preferably made of a material that is permeable to the hydrogen gas. This allows the hydrogen gas to pass through the wall of the passage tube 28 and into contact with the polymer 14. The passage tube is also preferably made of a material that is impermeable to the polymer 14, thus preventing the polymer 14 from entering into the interior of the passage tube 28. The passage tube 28 preferably opens into the interior of the tank body 12. The opening of the passage tube 28 is preferably covered with a filter 30 which prevents the polymer 14 from entering into the interior of the passage tube 28.

When the compressor 32 pumps hydrogen gas into the tank body 12, there is an increase of the hydrogen pressure inside the tank body 12. When the hydrogen pressure inside the tank body is increased, the polymer 14 is able to bind a greater amount of hydrogen. Preferably, the increase in pressure causes an increase in the number of Kubas interactions per metal center in the polymer 14.

When desired, hydrogen is preferably released from the system 10 as follows. The second valve 26 is opened, which allows hydrogen gas to flow out of the tank body 12 through the second opening 24. When hydrogen gas flows out of the tank body through the second opening 24, there is a decrease in pressure inside the tank body 12. When the pressure is decreased inside the tank body 12, the polymer 14 releases hydrogen. Preferably, the decrease in pressure causes a decrease in the number of Kubas interactions per metal center of the polymer 14.

Hydrogen that is released by the polymer 14 can flow out of the tank body 12 through the second opening 24. As shown in FIG. 4, the hydrogen flows through the second passage 22 to the fuel cell 36. The fuel cell 36 preferably uses hydrogen as a fuel and oxygen as an oxidant to produce electricity.

In an alternative embodiment, the system of the present invention preferably comprises a storage tank with a single opening. Hydrogen flows both into and out of the storage tank through the single opening. A valve is used to control the flow of hydrogen through the opening. The system is preferably portable. As such, the system can be transported to a filling station to be filled with hydrogen. After being filled with hydrogen, the system can then be transported to a site where the hydrogen energy is to be used. Applications for this system include, but are not limited to, vehicles, airplanes, homes, buildings, and barbeques.

EXAMPLE 1

Vanadium Hydrazide Materials

Preparation of Vanadium Hydrazide Samples

Chemicals were purchased from Aldrich and used as is.

Preparation of V(Mes)3.THF: To 50 ml of Mesitylmagnesiumbromide 1M (MesMgBr) in tetrahydrofuran (THF) was added 33.33 ml of THF. 6.22 g of VCl$_3$.3THF 97% was then added portion by portion. The obtained solution was stirred vigorously at room temperature for 2 hours after which a clear blue solution was obtained. 21.66 ml of dioxane was then added to the solution with stirring. After 2 more hours, stirring was ceased and the solution was left to settle before filtering. The filtrate was collected and concentrated in vacuum until crystals formed. 16.67 ml of diethyl ether was then added and the remaining product precipitated out. The solid product was then collected by filtration and washed several times with a solution of THF and ether (THF: ether=1:3 by volume) before drying in vacuum.

Preparation of Anhydrous Hydrazine: Pure Hydrazine was Prepared from hydrazine monohydrate by azeotropic distillation with toluene to remove water and avoid possible explosion. 100 ml of hydrazine monohydrate and 250 ml of toluene were added to a 500 ml one neck round bottom flask, equipped with a thermometer to measure the gas temperature. A water condenser was connected and followed by 2 flashes to collect the waste liquid and dry hydrazine. After distillation and removal of water 35 g of NaOH was added to the hydrazine-toluene flask and the hydrazine distilled under nitrogen.

Preparation of A100 and A150 vanadium hydrazide samples: The A100 sample was synthesized as follows: V(Mes)3.THF (3 g, 6.24 mmol) was dissolved in 75 ml of dry toluene at room temperature in an Erlenmeyer™ flask. 0.15 ml of hydrazine (0.15 ml, 4.68 mmol) was then added by syringe with vigorous stirring. The solution was stoppered and stirring was continued for 12 hours. The solution was then heated to 100° C. for 3 hours with stirring. After this, the system was filtered and a black solid was obtained. This solid was transferred to an air-free tube and was heated at room temperature under vacuum for 12 h, followed by heating at 60° C. for a period of 6 hours and another 6 hours at 100° C. The A150 sample was obtained by continuing heating the A100 at 150° C. for 6 hours in vacuum.

Preparation of B100 and B150 sample: the same procedure was followed as with the A100, and A150 samples, but with 0.20 ml of hydrazine.

Preparation of C100 and C150 sample: the same procedure was followed as with the A100, and A150 samples, but with 0.30 ml of hydrazine.

Preparation of D100 and D150 sample: the same procedure was followed as with the A100, and A150 samples, but with 0.40 ml of hydrazine.

A preferred mechanism of the reaction for the preparation of the vanadium hydrazide samples is set out in Scheme 1 below.

Scheme 1: Preferred Protonolysis Reaction Mechanism Leading to the Vanadium Hydrazide Product.

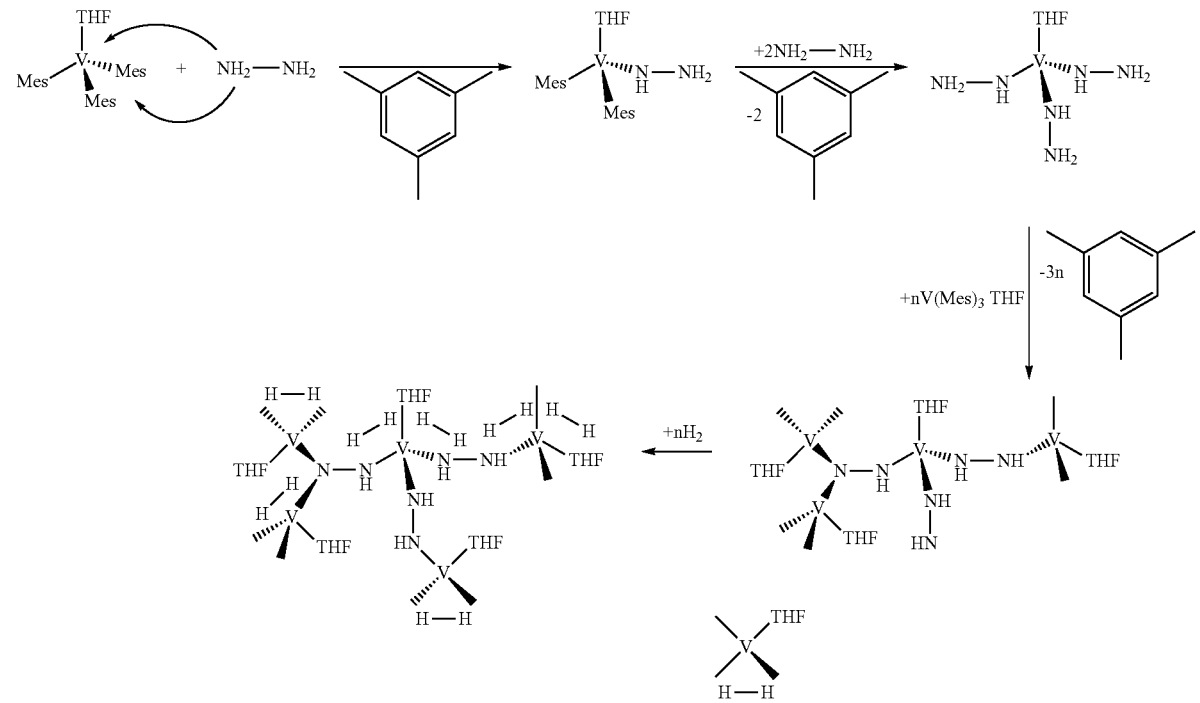

Powder X-Ray Diffraction (XRD) Studies

Powder X-ray diffraction (XRD) was performed on Siemens diffractometer D-500™ with Cu Kα radiation (40 KV, 40 mA) source. The step size was 0.02° and the counting time was 0.3 s for each step. Diffraction patterns were recorded in the 2θ range 2.3-52°. Samples for XRD analysis were put in a sealed capillary glass tube to protect sample from air and moisture during experiment.

Figure 5:
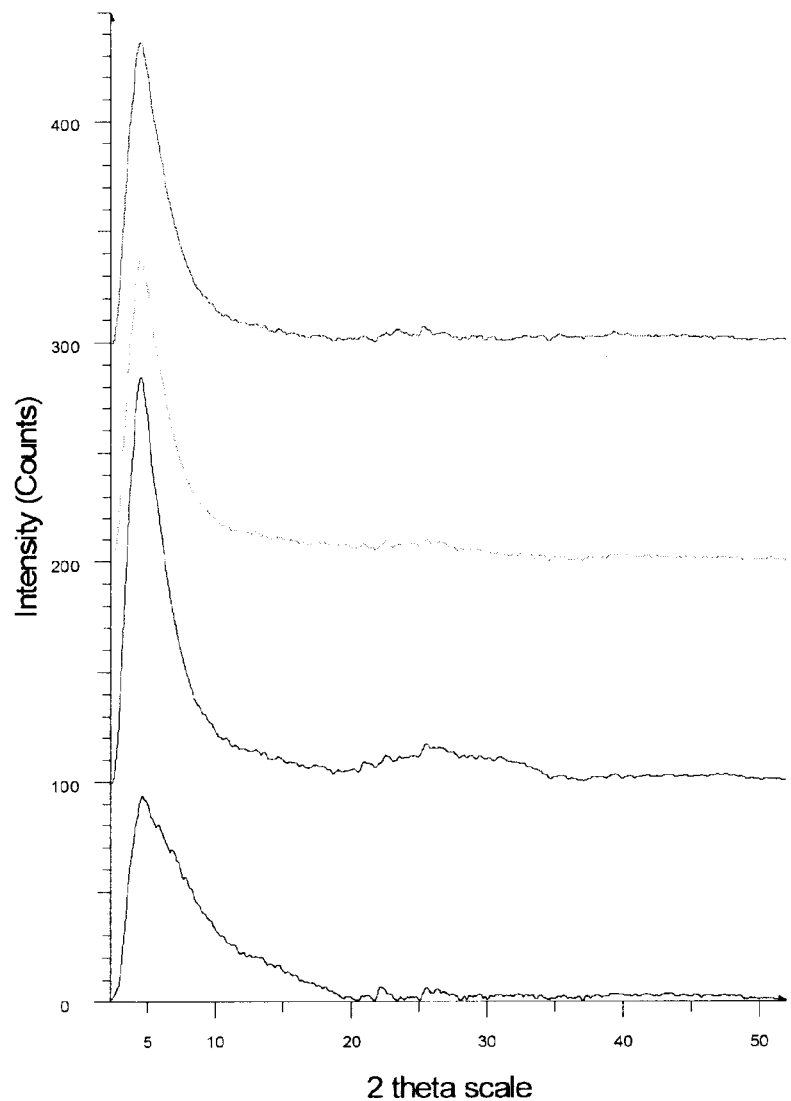
FIG. 5 shows the powder X-ray diffraction of vanadium hydrazide materials, specifically for A150, B150, C150, and D150 samples.

The powder x-ray diffraction (XRD) patterns for the vanadium hydrazide materials heated at 150° C. in vacuum are shown in FIG. 5. All patterns were similar and exhibit a single broad diffraction peak corresponding to a d$_{spacing}$ of 1.96 nm.

Figure 6:
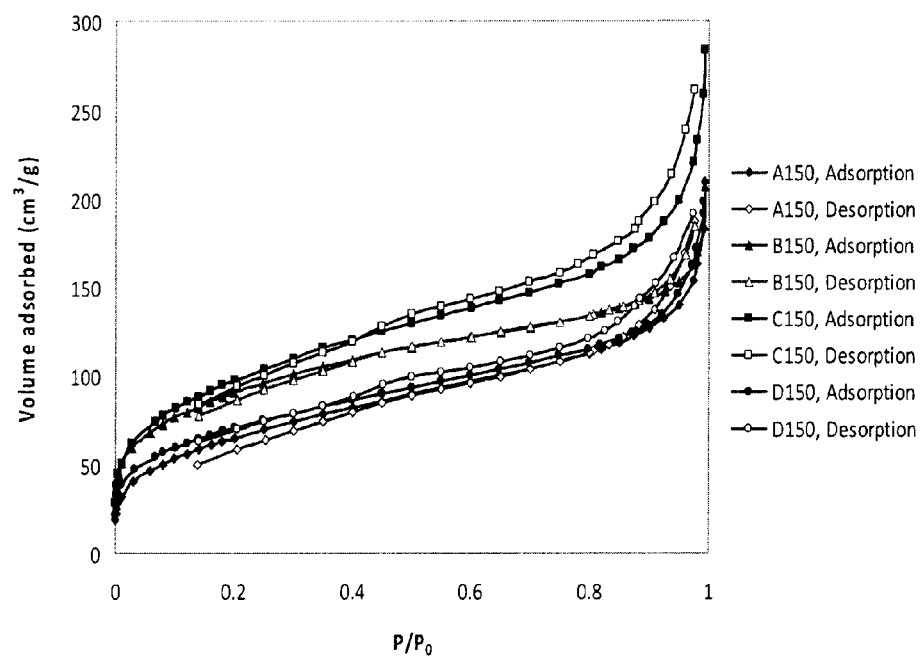
FIG. 6 shows nitrogen adsorption-desorption isotherms where the samples of vanadium hydrazide materials were measured on an ASAP-2010 instrument at 77K.

The position and broadness of this reflection suggests nanoscopic periodicity with a lack of long-range order. Nitrogen adsorption isotherms recorded at 77K are shown in FIG. 6. These isotherms confirm that these materials are microporous, with a small degree of mesoporosity, as reflected in the increase in volume adsorbed with pressure from 0.1 to 0.8 P/P$_0$. The specific surface areas of all materials decrease with increasing the drying temperature from 100 to 150° C. For example, C100 possesses a Brunauer-Emmett-Teller (BET) surface area of 524 m$^2$/g, but when heated in vacuum to 150° C., the surface area decreases to 348 m$^2$/g. The C, H, N, and V elemental analysis data of vanadium hydrazide materials are shown in table 1 and reflect the decreasing trend in carbon concentration with increasing hydrazine at 150° C., from 17.41 wt % to 2.8 wt %, consistent with a greater degree of elimination of arene with increased concentration of hydrazine. However, the carbon values are somewhat low due to carbide and nitride formation on combustion, leading to less than 100% for all elements present. Heating the sample leads to progressive arene elimination as monitored by IR spectroscopy (C—H stretch at 2950-2850 cm$^{-1}$), presumably by thermally driving the protolysis reaction between V(Mes)$_3$.THF and N$_2$H$_4$ further towards completion.

TABLE 1

C, H, N and V concentration of vanadium hydrazide materials.

| Sample | V(Mes)$_3$·THF/ N$_2$H$_4$ ratio | Vanadium (%) | Carbon (%) | Hydrogen (%) | Nitrogen (%) |
|---|---|---|---|---|---|
| A150 | 4/3 | 37.00 | 13.58 | 2.46 | 10.54 |
| B150 | 1/1 | 33.70 | 4.60 | 2.53 | 12.39 |
| C150 | 2/3 | 52.25 | 4.01 | 1.87 | 16.60 |
| D150 | 1/2 | 44.85 | 3.94 | 1.71 | 12.89 |

X-Ray Photoelectron Spectroscopy (XPS) Studies

Nitrogen adsorption and desorption data were collected on a Micromeritics ASAP 2010™. All X-ray Photoelectron Spectroscopy (XPS) peaks were referenced to the carbon C—(C, H) peak at 284.8 eV, and the data were obtained using a Physical Electronics PHI-5500™ spectrometer using charge neutralization. Elemental analysis was performed by Galbraith Labs, Knoxyille Tenn.

Figure 7:
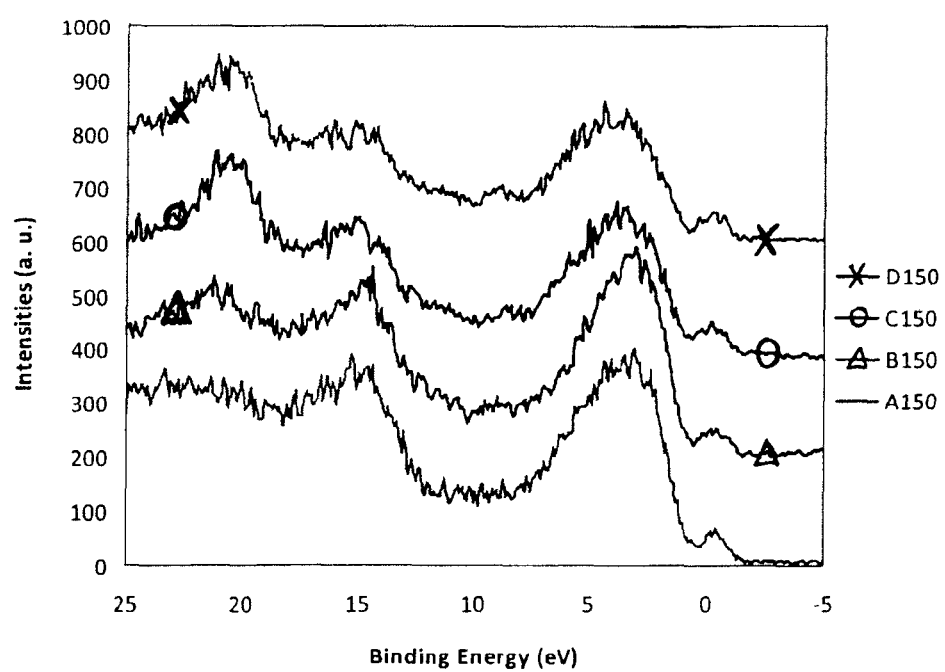
FIG. 7 shows the valence region of XPS spectrum of vanadium hydrazide materials heated to 150° C. with different ratios of hydrazine.
Figure 8:
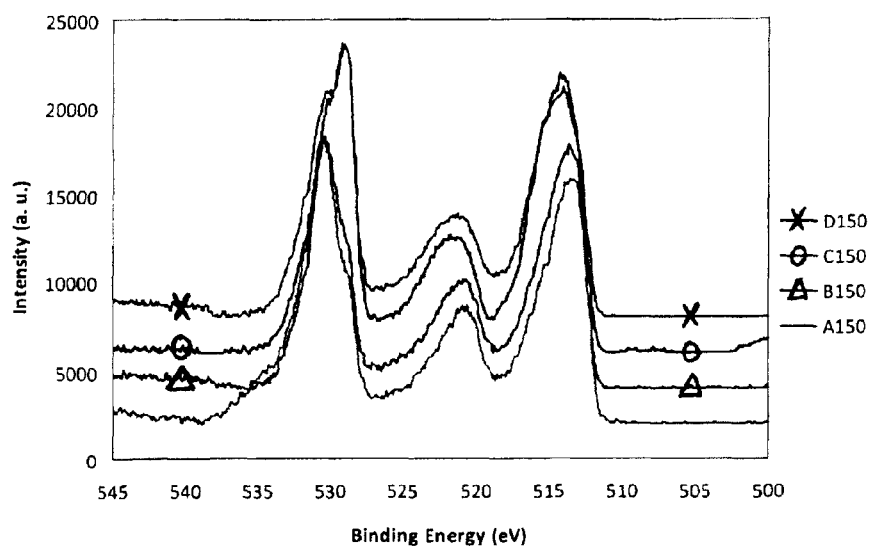
FIG. 8 shows the vanadium 2p1/2 and 2p3/2 and oxygen 1S region of XPS spectrum of vanadium hydrazide materials heated to 150° C. with different ratios of hydrazine.
Figure 9:
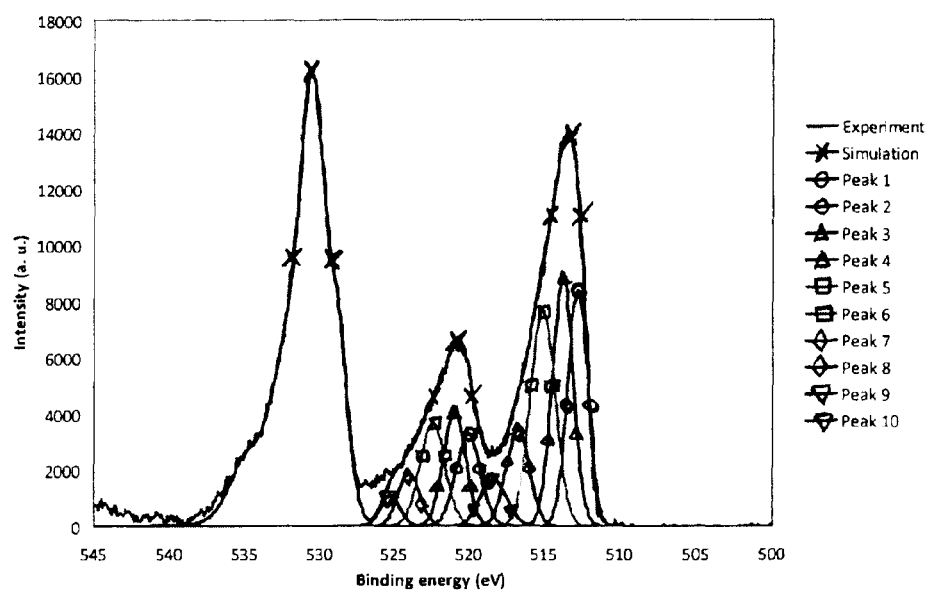
FIG. 9 shows the peak fitting of vanadium 2p1/2 and 2p3/2 emissions in the XPS spectrum of A150 sample of vanadium hydrazide materials.
Figure 10:
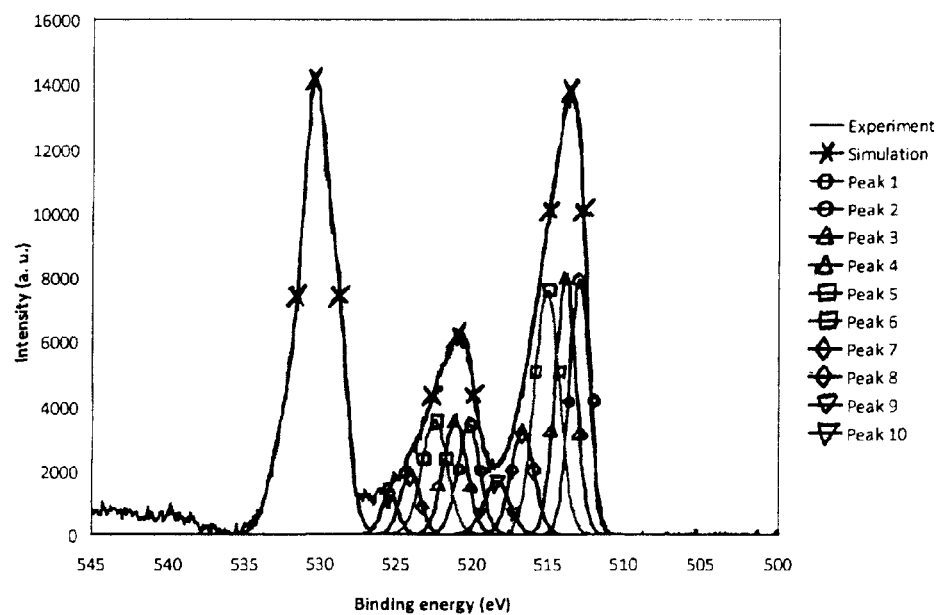
FIG. 10 shows the peak fitting of vanadium 2p1/2 and 2p3/2 emissions in the XPS spectrum of B150 sample of vanadium hydrazide materials.
Figure 11:
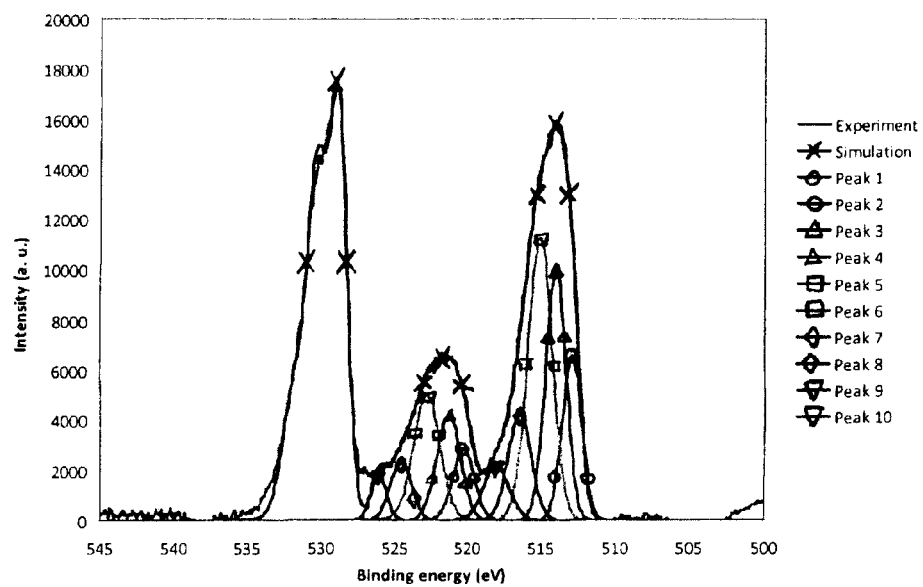
FIG. 11 shows the peak fitting of vanadium 2p1/2 and 2p3/2 emissions in the XPS spectrum of C150 sample of vanadium hydrazide materials.
Figure 12:
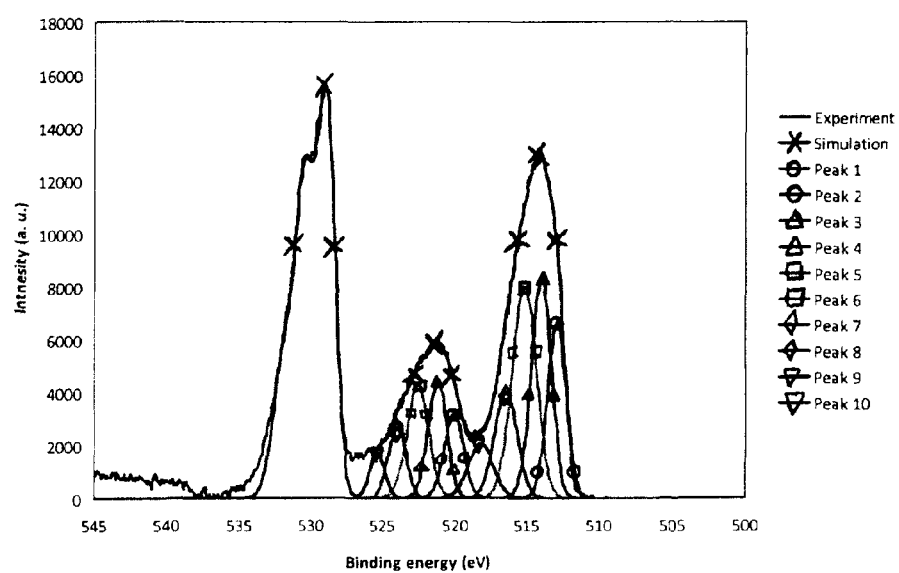
FIG. 12 shows the peak fitting of vanadium 2p1/2 and 2p3/2 emissions in the XPS spectrum of D150 sample of vanadium hydrazide materials.
Figure 13:
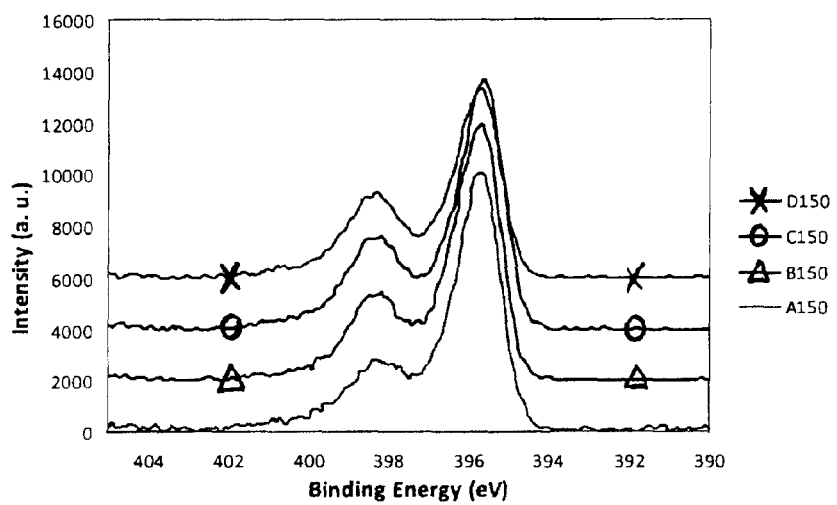
FIG. 13 shows the N 1S region of XPS Spectrum of vanadium hydrazide materials heated to 150° C. with different ratios of hydrazine.
Figure 14:
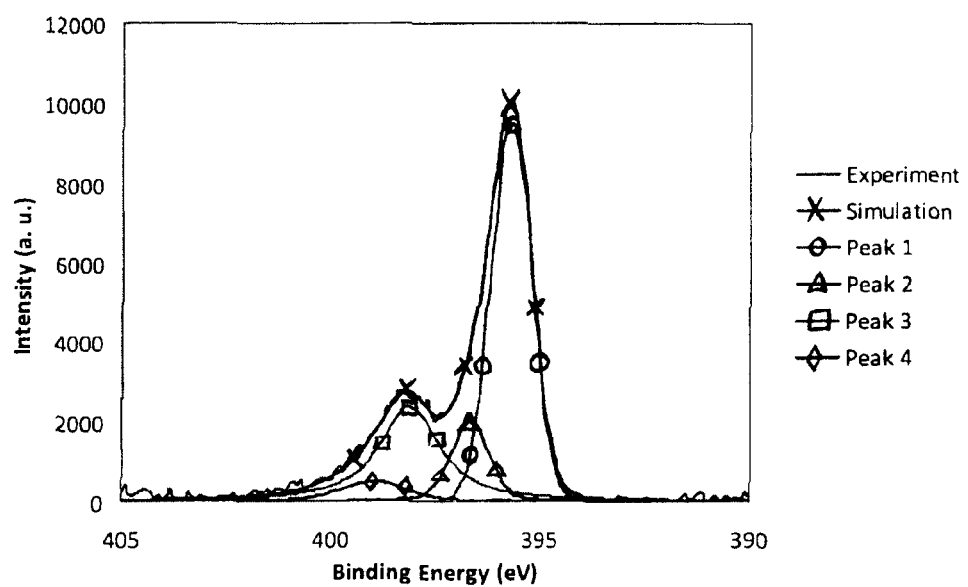
FIG. 14 shows the peak fitting of N 1S region of XPS Spectrum of A150 sample of vanadium hydrazide materials.
Figure 15:
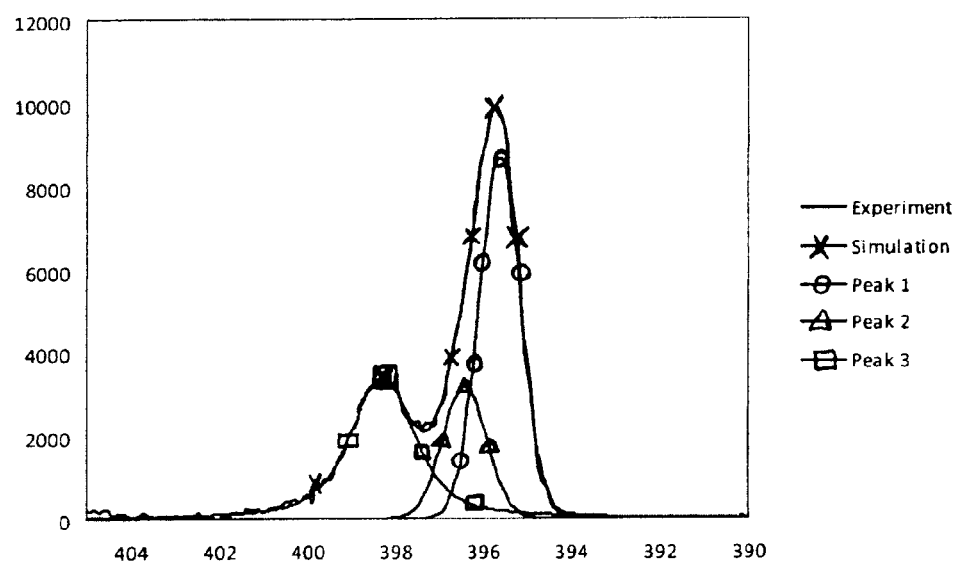
FIG. 15 shows the peak fitting of N 1S region of XPS Spectrum of B150 sample of vanadium hydrazide materials.
Figure 16:
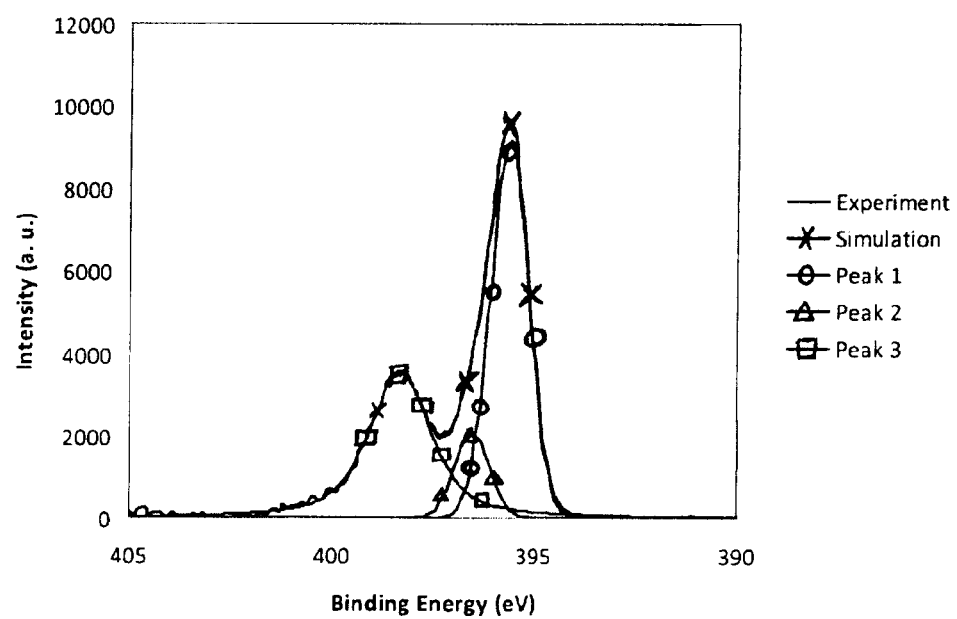
FIG. 16 shows the peak fitting of N 1S region of XPS Spectrum of C150 sample of vanadium hydrazide materials.
Figure 17:
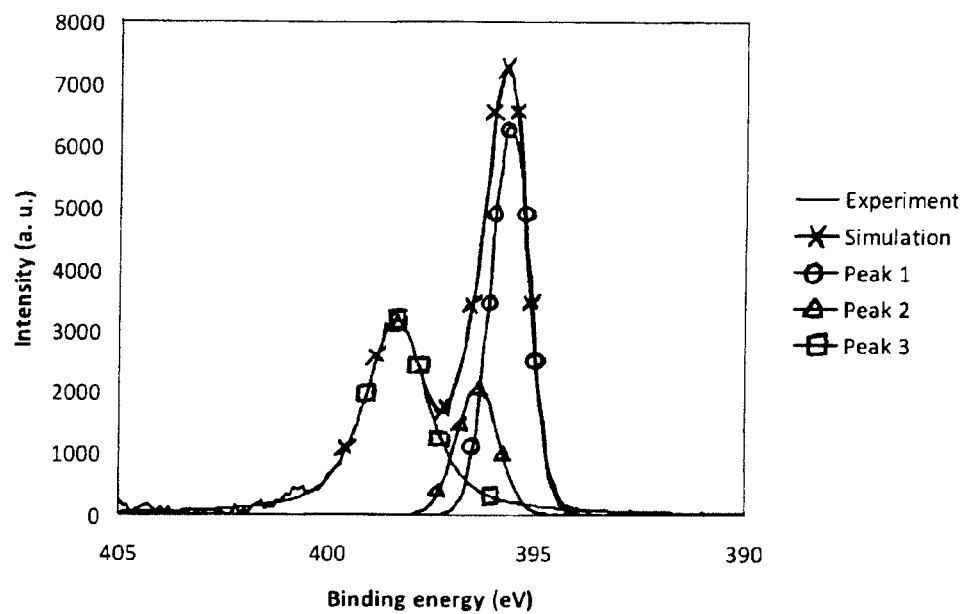
FIG. 17 shows the peak fitting of N 1S region of XPS Spectrum of D150 sample of vanadium hydrazide materials.

X-ray Photoelectron Spectroscopy (XPS) studies of the vanadium hydrazides were conducted and the results are shown in FIG. 7. No charge neutralization was required and emissions were observed at the Fermi level, suggesting that these materials are metallic. Multiple oxidation states of vanadium are detected in the vanadium 2p 1/2,3/2 region (FIGS. 8 to 12). By comparison with literature values, the emissions at 512.8 eV and 520.0 eV correspond to V(0), the emission at 513.8 eV and 520.9 eV can be assigned to a V(I) species, and the emissions at 515.0 eV and 522.3 eV represents V(III), while the emissions at 516.4 eV and 523.8 eV correspond to V(IV). The appearance of multiple oxidation states both lower and higher than the V(III) starting material is consistent with disproportionation, common with V, as no net oxidation or reduction of the V (III) starting material has occurred. The XPS spectra of all materials in the N Is region exhibit a broad emission centered at 396 eV with a shoulder at 398.5 eV which can be simulated as 3 major peaks (FIGS. 13 to 17). The first simulated emission located at 395.6 eV likely corresponds to an NH nitrogen bound directly to V. The second emission located at 396.4-396.6 eV likely represents unbound terminal —NH$_2$ species, while the third emission at 398 eV can be assigned to quaternary hydrazinium species. The A150 sample has another simulated peak at 398.8 eV, possibly corresponding to bound NH$_3$, which may be the product of a redox reaction between N$_2$H$_4$ and V(Mes)$_3$.THF, or another bound hydrazine species. There is also evidence for bound THF in the XPS from the oxygen region (FIGS. 8 to 12), as indicated by the high intensity emissions centered at 530.4 eV. The difficulty removing THF is not surprising due to the well-documented high oxophilicity of early transition metals.

Hydrogen Adsorption Measurements

Hydrogen adsorption isotherms were obtained by using a computer controlled commercial Gas Reaction Controller™ manufactured by Advanced Materials Corporation, Pittsburgh, Pa. High purity hydrogen (99.9995% purity) was used as the adsorbent. Hydrogen storage measurements on a standard AX-21 sample (4.5 wt. %) were performed to ensure proper calibration and functioning of the instrumentation. Leak testing was also performed during each measurement by checking for soap bubbles at potential leak points. These measurements are necessary to ensure the veracity of the isotherms. In the H$_2$ adsorption-desorption experiments complete reversibility was observed for all samples across the whole range of pressures. Samples were run at liquid nitrogen temperature (77K), liquid argon temperature (87K), and room temperature (298K) to 8.5 MPa. Isotherms were always measured first at room temperature and then at 77 K or 87 K and the temperature is kept constant by keeping the sample chamber in liquid N$_2$, liquid Ar, or water. The skeletal density was measured using a Quantachrome Ultrapycnometer™. When the skeletal density is used for the hydrogen uptake measurement, the compressed hydrogen within the pores is treated as part of the sample chamber volume and hence subtracted. Therefore only the hydrogen physisorbed to the walls of the structure will be recorded by the PCI instrument as the adsorption capacity of the material. Gravimetric densities are recorded as read from the isotherms while volumetric densities are calculated using the skeletal density from the pychnometer and the gravimetric density. The results are shown in Table 2.

TABLE 2

Summary of excess storage results on vanadium hydrazide materials and carbon AX-21. Data are taken at 85 bar.

| Material | BET Surface Area (m$^2$/g) | Skeletal Density (g/cm$^3$) | Gravimetric Adsorption (wt. %) | Volumetric Adsorption (kg/m$^3$) | Retention (%) |
|---|---|---|---|---|---|
| A100 | 268 | 1.9174 | 2.08 (at 77 K) | 40 (at 77 K) | 40 |
| | | | 0.84 (at 298 K) | 16.1 (at 298 K) | |
| A150 | 242 | 2.3795 | 1.66 (at 77 K) | 39.5 (at 77 K) | 41 |
| | | | 0.68 (at 298 K) | 18.2 (at 298 K) | |
| B100 | 378 | 2.1640 | 2.22 (at 77 K) | 48 (at 77 K) | 32 |
| | | | 0.70 (at 298 K) | 15.2 (at 298 K) | |

TABLE 2-continued

Summary of excess storage results on vanadium hydrazide materials and carbon AX-21. Data are taken at 85 bar.

| Material | BET Surface Area (m²/g) | Skeletal Density (g/cm³) | Gravimetric Adsorption (wt. %) | Volumetric Adsorption (kg/m³) | Retention (%) |
|---|---|---|---|---|---|
| B150 | 329 | 2.2000 | 1.50 (at 77 K) | 33 (at 77 K) | 29 |
|  |  |  | 0.43 (at 298 K) | 9.5 (at 298 K) |  |
| C100 | 524 | 2.1557 | 2.88 (at 77 K) | 62 (at 77 K) | 37 |
|  |  |  | 1.07 (at 298 K) | 23.1 (at 298 K) |  |
| C150 | 348 | 1.9792 | 4.04 (at 77 K) | 80 (at 77 K) | 29 |
|  |  |  | 1.17 (at 298 K) | 23.2 (at 298 K) |  |
| D100 | 307 | 2.0413 | 3.87 (at 77 K) | 79 (at 77 K) | 22 |
|  |  |  | 0.84 (at 298 K) | 17.2 (at 298 K) |  |
| D150 | 256 | 2.4125 | 2.48 (at 77 K) | 60 (at 77 K) | 28 |
|  |  |  | 0.70 (at 298 K) | 16.9 (at 298 K) |  |
| AX-21 | 3225 | 2.103 | 4.2 (at 77 K, 65 bar) | 14 (at 77 K, 65 bar) | 13 |
|  |  |  | 0.55 (at 298 K) | — |  |

Enthalpies of adsorption were calculated using a variant of the Clapeyron-Clausius I equation taking both 77K and 87K hydrogen adsorption data.

$$\ln\left(\frac{P_1}{P_2}\right) = \Delta H_{ads} \cdot \frac{T_2 - T_1}{R \cdot T_2 \cdot T_1} \quad (1)$$

Where $P_n$=pressure for isotherm n, $T_n$=temperature for isotherm n, R: gas constant.

Pressure as a function of the amount adsorbed was determined by using exponential fit for each isotherm; the first 10-11 points of the isotherms were picked up and fit to the exponential equation. This exponential equation gives an accurate fit over the pressure up to 1 MPa with the goodness of fit ($R^2$) above 0.99. The corresponding $P_1$ and $P_2$ values at a certain amount of $H_2$ adsorbed at both temperatures can be obtained by the simulated exponential equation. Inputting these numbers into equation 1, the adsorption enthalpies are calculated.

Figure 18:
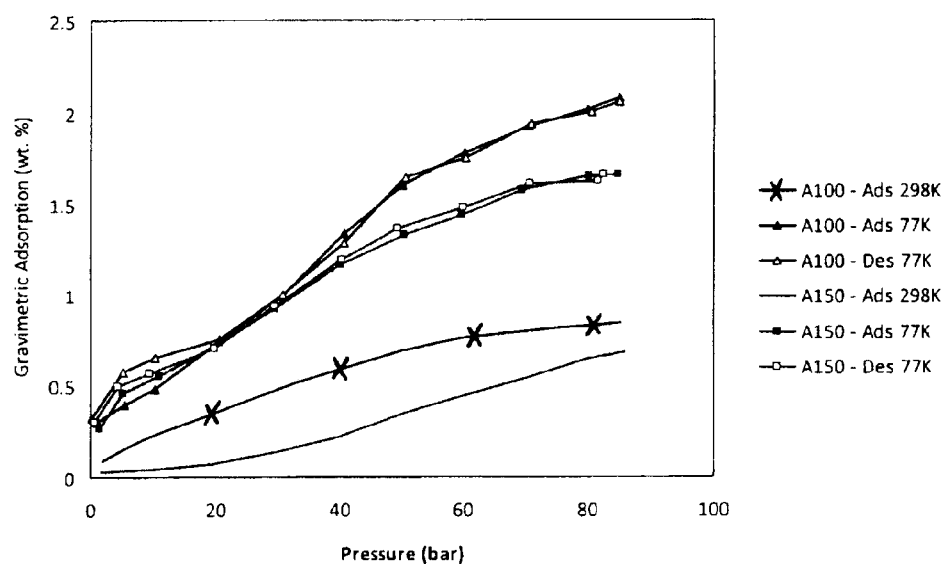
FIG. 18 shows the hydrogen adsorption-desorption excess storage isotherms of A-series vanadium hydrazide materials synthesized with a V:hydrazine ratio of 4:3.
Figure 19:
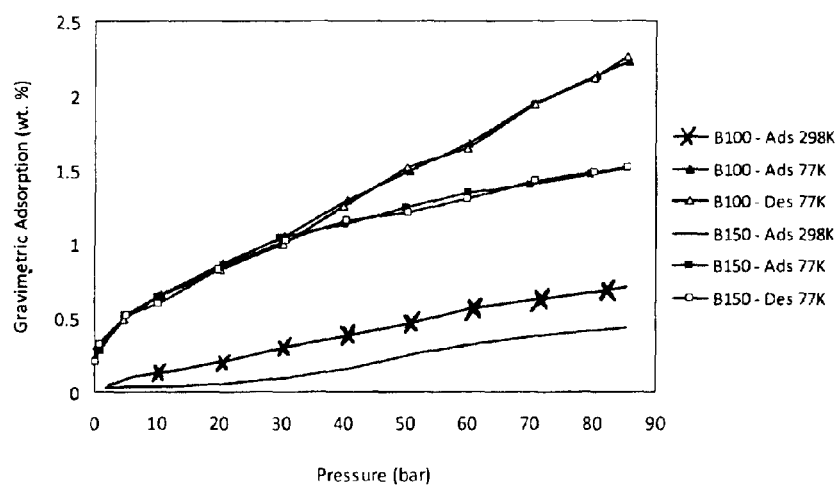
FIG. 19 shows the hydrogen adsorption-desorption excess storage isotherms of B-series vanadium hydrazide materials synthesized with a V:hydrazine ratio of 1:1.
Figure 21:
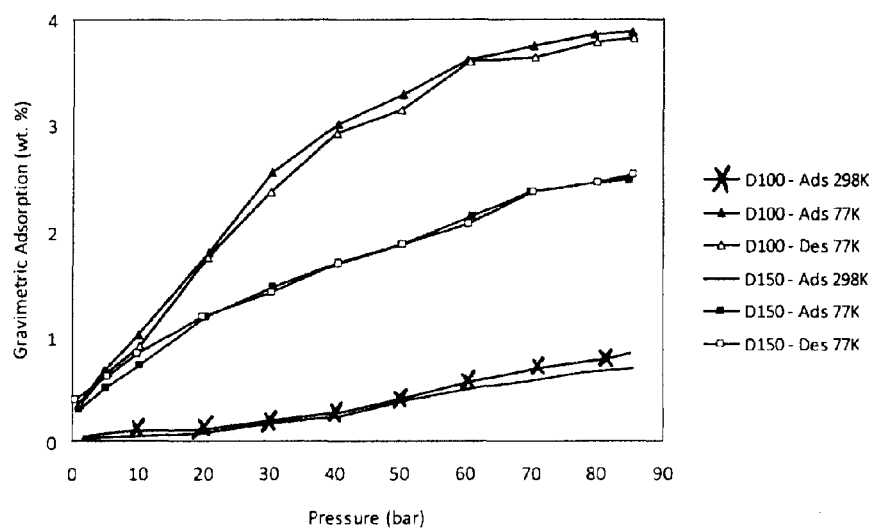
FIG. 21 shows the hydrogen adsorption-desorption excess storage isotherms of D-series vanadium hydrazide materials synthesized with a V:hydrazine ratio of 1:2.

The excess storage isotherms of A100 and A150 samples are shown in FIG. 18. The excess storage isotherms of B100 and B150 samples are shown in FIG. 19. The excess storage isotherms of D100 and D150 samples are shown in FIG. 21.

Figure 20:
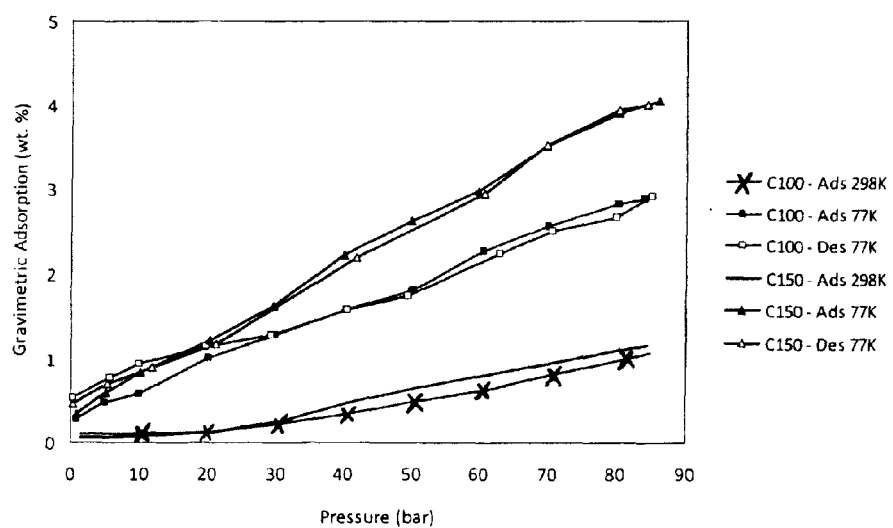
FIG. 20 shows the hydrogen adsorption-desorption excess storage isotherms of C-series vanadium hydrazide materials synthesized with a V:hydrazine ratio of 1:1.5.

The excess storage isotherms of C100 and C150 samples are shown in FIG. 20. At 77 K these isotherms show an initial rise at low pressure consistent with a small amount of physisorption expected from the surface areas in the 200-500 m²/g range, followed by a linear region which only begins to reach saturation in the D series of these samples. At room temperature there is very little adsorption until 30 bar, after which a linear region emerges. Linear behavior is not typical of physisorption and suggests a different mechanism of hydrogen storage is operative in this region. The gravimetric and volumetric adsorption of C150 sample is 1.17 wt. % at 85 bar and 298K, with a volumetric density of 23.2 kg $H_2$/m³. This value is over three times that of compressed gas under the same conditions. At 77K, this sample adsorbs 4.04 wt. %, and 80 kg $H_2$/m³. The sample D100 demonstrates 3.87 wt. % and 79 kg/m³, which is almost as high as the performance of C150 under the same conditions. But at room temperature, this sample has smaller adsorption capacity, just 0.84 wt. % which corresponds to 17.2 kg/m³. These results at 77K surpass the Ultimate DOE goal of 70 kg/m³, however at a much lower temperature, and approach the DOE 2010 at room temperature of 28 kg/m³. This volumetric performance is much greater than that of MOF-177 and NOTT-112, which show 48.0 and 50.3 kg/m³ at 77 K, respectively, at this pressure. By comparing the gravimetric adsorption at 298K and 77K, the retentions of excess adsorption capacities can be calculated, and range from 41% down to 22%. This is much higher than that of MOF-5 and carbon AX-21, which retain 22.2% and 13.2%, respectively, and also indicates a different mechanism than simple physisorption. From these results, the molar ratio of 2:3 and the heating temperature of 150° C. is the optimal synthesis conditions for hydrogen adsorption performance. The elemental analysis results show that lower hydrazine ratios of 1:1 and 4:3 are not sufficient to remove enough alkyl groups to ensure high activity by reducing the steric profile around the metal center and lowering the system weight through substitution of mesitylene for hydrazine, but the highest ratio of 2:1 leads to a material in which saturation is reached at 80 bar. This is consistent with excess hydrazine blocking coordination sites that would otherwise be available for $H_2$. Another trend is that the higher heating temperature of 150° C. causes an increase in skeletal densities and decreases of gravimetric adsorption capacities of all samples except for the C100 sample. The increase in density is likely due to the elimination of alkyl groups, a process which was monitored by observation of the C—H stretch in the IR. Another positive effect of heating is the reducing of adsorption-desorption hysteresis at 0-20 bar pressure which appear at all samples heated at 100° C. and disappear at all the samples heated at 150° C. This hysteretic effect also diminishes with decreasing V(Mes)$_3$.THF/N$_2$H$_4$ reaction ratio. Calculations on the basis of gravimetric adsorption and the vanadium content in each sample result in an average number of hydrogen molecules per vanadium atom (table 3) ranging from 1.13-1.96 $H_2$/V at 77K and 0.32-0.57 $H_2$/V at 298K. These are lower than the values observed for silica-supported titanium and chromium species, but comparable with that of silica supported V fragments which show 1.73 $H_2$/V under these same conditions. The reason for this is likely due inhomogeneity in the hydrazide gel resulting in poor $H_2$ binding to the V(IV) and V(V) centers detected by XPS or steric inaccessibility of many of the V centers.

TABLE 3

Average number of hydrogen molecule adsorbed on each vanadium site at 85 bar.

| Sample | Number of $H_2$/V at 77 K | Number of $H_2$/V at 298 K |
|---|---|---|
| A150 | 1.14 | 0.47 |
| B150 | 1.13 | 0.32 |

TABLE 3-continued

Average number of hydrogen molecule adsorbed on each vanadium site at 85 bar.

| Sample | Number of $H_2$/V at 77 K | Number of $H_2$/V at 298 K |
|---|---|---|
| C150 | 1.96 | 0.57 |
| D150 | 1.41 | 0.40 |

Figure 22:
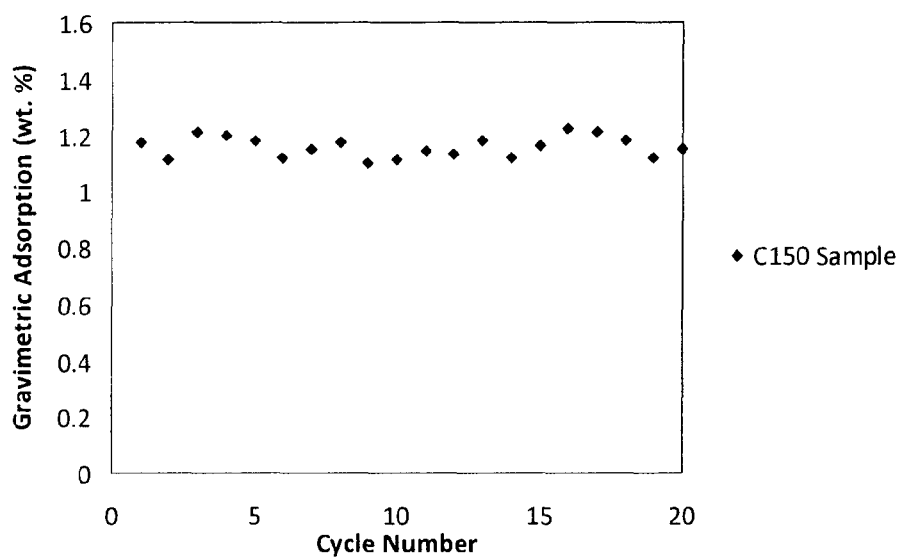
FIG. 22 shows the hydrogen adsorption capacity at 298K in a 20 cycle test of the C150 sample.
Figure 23:
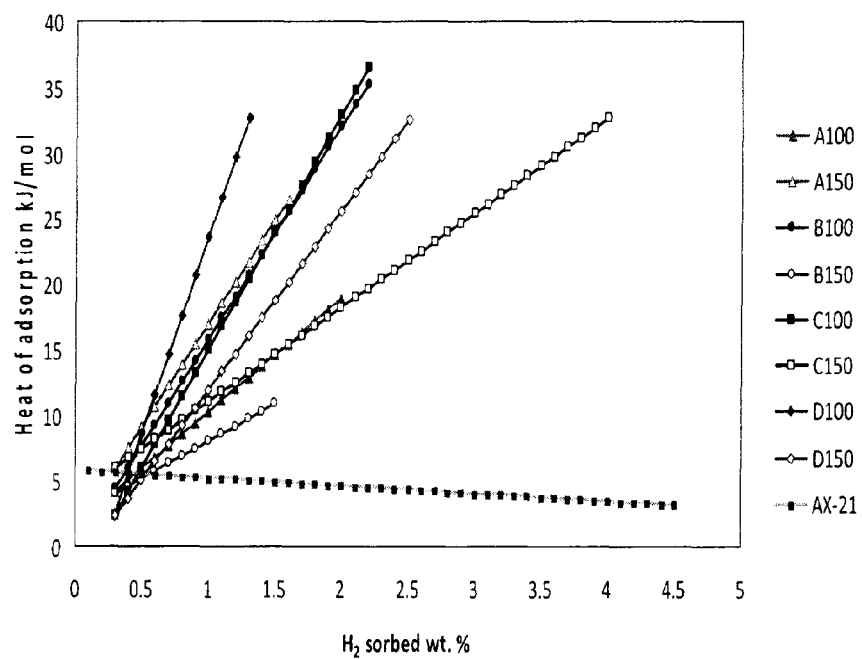
FIG. 23 shows the heat of hydrogen adsorption on vanadium hydrazide materials and on carbon AX-21.

A 20 cycle run at 298K with pressure up to 85 bar was carried out on C150 sample. The results show no significant loss of excess adsorption capacity through cycling (FIG. 22). By fitting the adsorption isotherms at 77K and 87K into the Clapeyron-Clausius equation, the isosteric heats of hydrogen adsorption can be calculated. The data for materials heated at 100° C. and 150° C., as well as that of carbon AX-21 as a standard were measured under the same conditions (FIG. 23). This isoteric heat of adsorption of all vanadium hydrazide materials rises from roughly 3-5 kJ/mol $H_2$ up to 36.5 kJ/mol $H_2$, contrasting strongly to the behavior of AX-21, which has enthalpies which decrease from 6 kJ/mol $H_2$ down to 3.3 kJ/mol $H_2$, typical of physisorption. The average value of the vanadium hydrazides falls in the range of 20-30 kJ/mol $H_2$, believed to be the ideal heat of hydrogen adsorption of suitable room temperature hydrogen storage materials. The rising enthalpies with surface coverage were observed in previous publications from our group concerning hydrogen storage on supported organometallic fragments. More research and theroretical studies beyond the scope of this paper are needed to clarify this rising trend, however these heats of adsorption and the linear regions of the isotherms suggest a different adsorption mechanism from physisorption ($\Delta H=4-13$ kJ/mol $H_2$) and metal hydride formation ($\Delta H \geq 70$ kJ/mol $H_2$) likely involving the Kubas interraction.

Electron Paramagnetic Resonance (EPR) Spectroscopic Studies

EPR spectra were collected at room temperature using a Bruker EMXplus X-band™ (~9.4 GHz) spectrometer. Samples were placed in 4 mm outer-diameter quartz tubes sealed with 'O' ring needle valves. Sample volumes were ~300 µL. To produce hydrogen loaded samples, hydrogen gas (grade 6) was applied directly, at a pressure of 1 atmosphere, to the sample within the EPR tube using an air-tight purge valve to ensure an inert environment.

Figure 24:
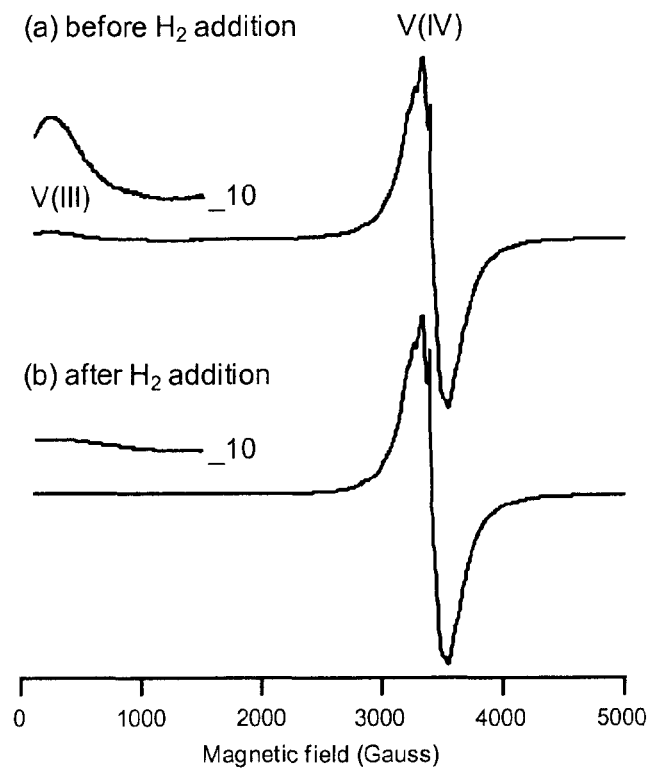
FIG. 24 shows the room-temperature EPR spectra of vanadium hydrazide gel C150 both: (a) prior to exposure to hydrogen gas, and (b) after exposure to hydrogen gas.

In order to obtain a deeper understanding of the nature of hydrogen binding, electron paramagnetic resonance (EPR) spectroscopic measurements were conducted on the C150 sample before and after hydrogen loading. Prior to hydrogen addition, the X-band (9.4 GHz) EPR spectrum at room temperature shows a strong signal centered at 3411 G (g=1.96), diagnostic of a V(IV) center(3d1, S=½), with characteristic partially resolved hyperfine splittings (51V, I=7/2, isotopic abundance=99.75%) (FIG. 24(a)). A second paramagnetic species was also observed, exhibiting a broad low-field peak (270 G), corresponding to a V(III) center (3d2, S=1). EPR measurements of such species have been reported relatively infrequently, due to difficulties in measuring spectra from V(III) "non-Kramers" integer spin systems. Commonly, the zero-field splitting (zfs) of V(III) complexes is much larger than the microwave quantum used in EPR experiments (~0.3 cm$^{-1}$ for X-band EPR) so that normally allowed transitions ($\Box MS=\pm 1$) are no longer within the field/frequency range of conventional spectrometers. However, in high symmetry systems the zfs is relatively small, permitting normally allowed transitions to be observed, as in the experiments described here, however the intensity of such resonances are often lower than expected. This explains why the XPS shows a much higher relative proportion of V(III) to V(IV). After hydrogen gas was added to the sample, the EPR signal from the V(III) species was reduced in intensity by ~90% (FIG. 24(b)). This observation is consistent with the lowering of symmetry at the V(III) center caused by hydrogen binding (Scheme 1), which increases the zfs, resulting in a new "EPR silent" species. Since very little hydrogen is adsorbed at ambient pressure, it is likely that the on-off equilibrium, which favors the gas phase at lower pressures, is enough to perturb this signal on the EPR time scale. By contrast, the signal from the V(IV) center was unchanged both in shape nor intensity, indicating that hydrogen binding occurs preferentially with the vanadium ions in the 3+ oxidation state in C150. Removing the hydrogen leads to a restoration in the intensity of the signal for V(III). These observations are consistent with weak and reversible chemisorption via the Kuhas interaction to the V(III) centers.

EXAMPLE 2

Titanium Hydrazide Materials

Preparation of Titanium Hydrazide Samples

The following procedure was used to prepare tribenzyltitanium and tetrabenzyltitanium. All solvents used in this procedure were distilled in nitrogen gas before they were used.

1. A solution of $TiCl_4$ (10 ml, 91.2 mmol) in heptane (100 ml) was added to a solution of $C_6H_5CH_2MgCl$ (400 ml, 1M in diethyl ether, 4 equiv.) at −15° C. dropwise over 2 hours. The mixture was stirred for 3 hours at −15° C. and filtered through Celite™.

2. The solid residue was washed with diethyl ether (2×50 ml) and the combined filtrate and washings were reduced in vacuum.

3. The residue was dissolved in heptane (50 ml) and filtered. This was followed by further washing of the residue with heptane (2×50 ml).

4. The filtrate and heptane washings were combined and concentrated (ca. 70 ml), and cooled to −30° C. overnight to yield a dark red tetrabenzyltitanium crystalline produce. The yield was 50% to 60%. The heptane was evaporated in a vacuum glove box.

5. Ethyllithium (1 equivalent) was added to the tetrabenzyltitanium in toluene at 0° C. The mixture was stirred for 2 hours.

6. The dissolved part of the benzyllithium formed was precipitated by carboxylation at −78° C. by the slow input of dry carbon dioxide gas.

7. Tribenzyltitanium solution was obtained after filtration in 65% yield with respect to the initial tetrabenzyltitanium.

The following procedure was used to prepare a titanium hydrazide sample using the tribenzyltitanium described above. All solvents used in this procedure were distilled in nitrogen gas before they were used.

1. A solution of hydrazine was added directly to a solution of tribenzyltitanium at room temperature, and allowed to react overnight.

2. The solid residue of a titanium hydrazide sample was obtained by vacuum supply.

Figure 25:
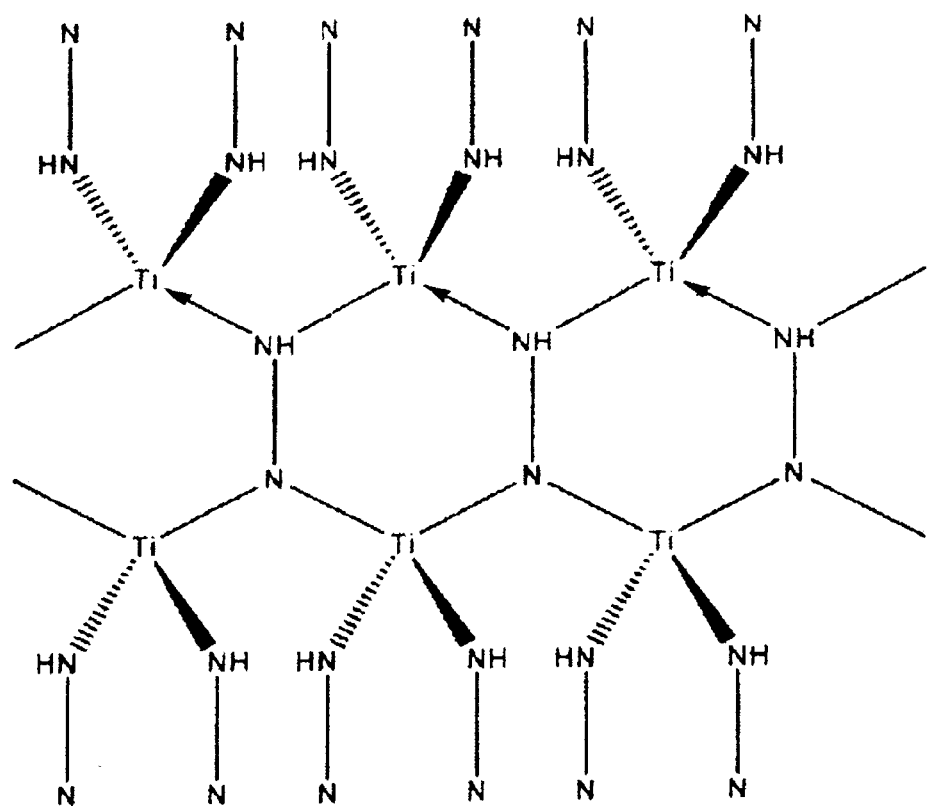
FIG. 25 illustrates a preferred embodiment of the novel polymers of the present invention.

An example of a titanium hydrazide polymer obtained by this procedure is shown in FIG. 25.

The following procedure was used to prepare a titanium hydrazide sample using tetrabenzyltitanium.

1.3 g of tetrabenzyltitanium was dissolved in 100 ml of toluene.

2. 0.17 ml of hydrazine was added to the tetrabenzyltitanium solution at room temperature with stirring. The reaction was allowed to take place overnight.

3. The solution was heated to nearly 50° C. for 7 hours.

4. The solution was filtered to obtain a precipitate product. The precipitate product was black and had a weight of 24.26 g.

5. The precipitate product was placed in a vacuum glove box. A gel powder of a titanium hydrazide sample was obtained. The weight of the gel powder was 19.37 g.

Figure 27B:
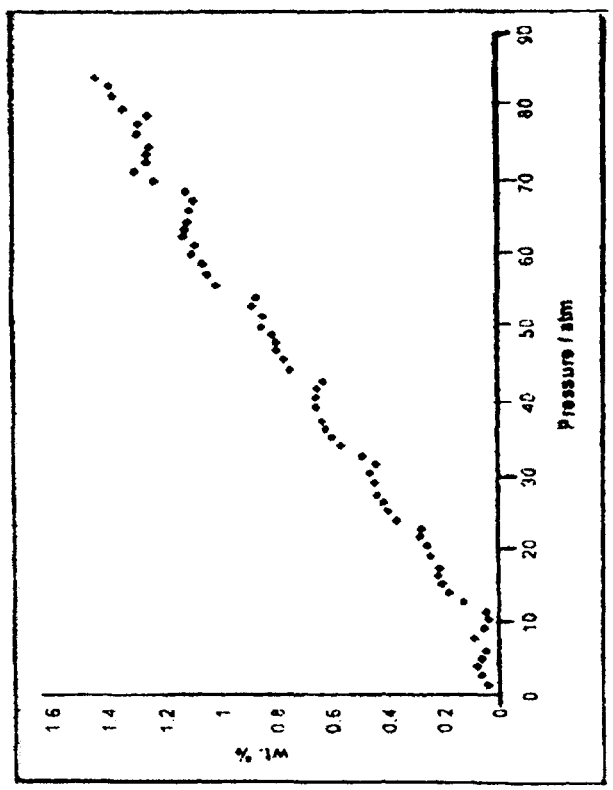
FIG. 27 shows: (a) a preferred embodiment of the novel intermediate titanium compounds of the present invention; and (b0 the hydrogen adsorption-desorption isotherm of a preferred titanium hydrazide material obtained using this preferred intermediate compound.
Figure 27A:
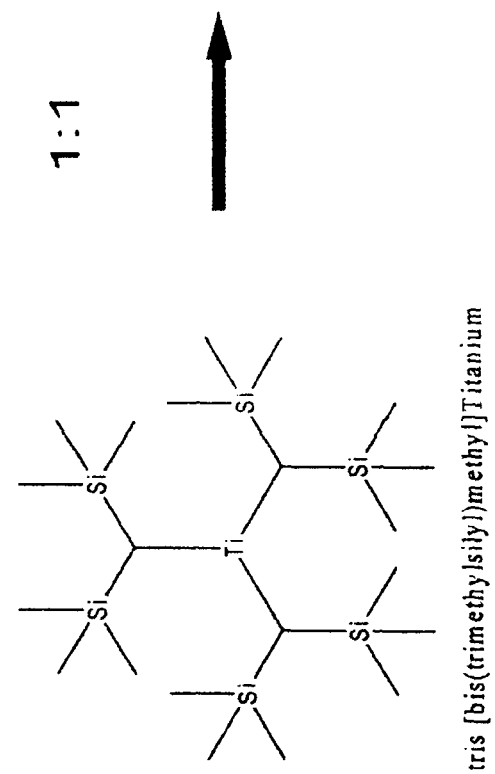

The following procedure was used to obtain tris [bis(trimethylsilyl)methyl]titanium, which was then used to obtain a titanium hydrazide sample. Tris[bis(trimethylsilyl)methyl]titanium is shown in FIG. 27($a$).

1. 2 g of $TiCl_3$ $(Et_3N)_2$ was dissolved in 34 ml of ether solution.

2. 2.8 g of bis(trimethylsilyl)methyl-lithium was dissolved in 42 ml of ether solution.

3. The solution of bis(trimethylsilyl)methyl-lithium was added dropwise into the $TiCl_3$ $(Et_3N)_2$ solution at −60° C.

4. The resulting solution was slowly warmed to room temperature for 2 hours.

5. All solvent was removed by vacuum.

6. 30 ml of toluene was added to redissolve the materials. The solution was filtered to remove LiCl.

7. A product of tris[bis(trimethylsilyl)methyl]titanium was obtained.

8. 0.18 ml of hydrazine was added to the tris [bis(trimethylsilyl)methyl]titanium to obtain a titanium hydrazide sample.

Hydrogen Adsorption Measurements

Hydrogen adsorption-desorption isotherms for the above-mentioned titanium hydrazide samples were obtained using a computer controlled commercial gas reaction controller. Gravimetric adsorption of a sample can be read from the isotherm. Volumetric adsorption can be calculated from the gravimetric adsorption and the skeletal density. The skeletal density was measured by a pycnometer.

A first sample and a second sample of titanium hydrazide were prepared by reacting tribenzyltitanium with hydrazine in a 4 Ti:3 hydrazine ratio using the procedure described above.

The first sample of titanium hydrazide was dried at 100° C. The first sample was measured by a pycnometer to have a skeletal density of 1.03 g/cm$^3$. The hydrogen adsorption-desorption isotherm for this sample is shown in FIG. 26($a$).

The second sample of titanium hydrazide was dried at 150° C. The second sample was measured by a pycnometer to have a skeletal density of 2.44 g/cm$^3$. The hydrogen adsorption-desorption isotherm for this sample is shown in FIG. 26($b$).

As shown in FIG. 26($b$), the second sample of titanium hydrazide has a gravimetric adsorption of about 5 wt % at a temperature of 298 K. The volumetric adsorption of the second sample of titanium hydrazide was calculated to be about 150 kg/m$^3$ at 298 K.

For both the first sample and the second sample, a linear relationship between the pressure and the gravimetric adsorption was observed. An increase in pressure is accompanied by an increase in gravimetric adsorption. Furthermore, complete reversibility of hydrogen adsorption was observed for both the first sample and the second sample across the whole range of pressures at room temperature.

A third sample and a fourth sample of titanium hydrazide were prepared by reacting tris[bis(trimethylsilyl)methyl]titanium with hydrazine in a 1 Ti:1 hydrazine ratio using the procedure described above.

The third sample of titanium hydrazide was dried at 25° C. The third sample was measured by a pycnometer to have a skeletal density of 2.32 g/cm$^3$. The hydrogen adsorption-desorption isotherm for this sample is shown in FIG. 27($b$).

The gravimetric adsorption of the third sample increases with an increase in pressure. The volumetric adsorption of the third sample of titanium hydrazide was calculated to be about 35 kg/m$^3$.

Figure 28:
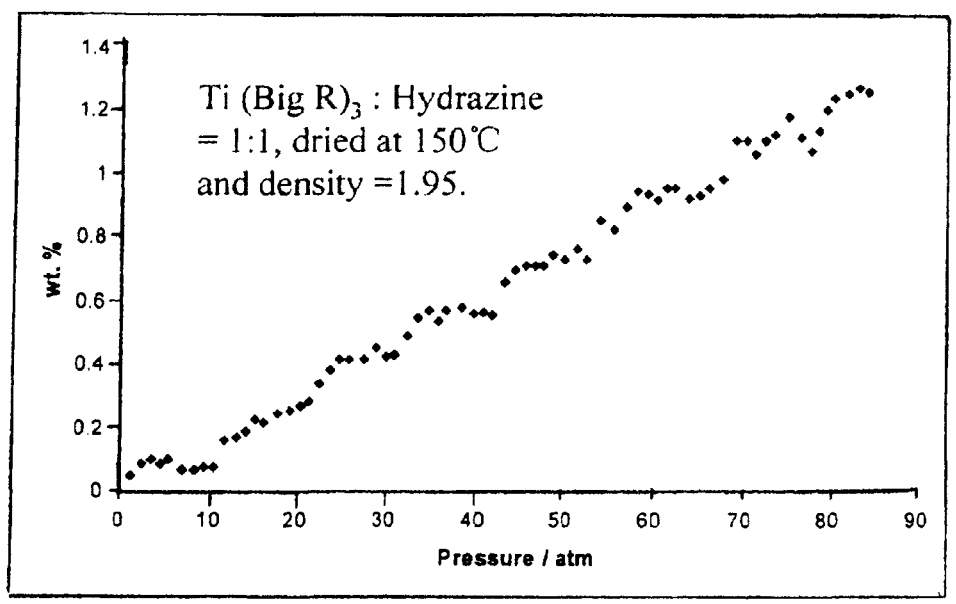
FIG. 28 shows the hydrogen adsorption-desorption isotherm of a preferred titanium hydrazide material.

The fourth sample of titanium hydrazide was dried at 150° C. The fourth sample was measured by a pycnometer to have a skeletal density of 1.95 g/cm$^3$. The hydrogen adsorption-desorption isotherm for this sample is shown in FIG. 28.

The gravimetric adsorption of the fourth sample increases with an increase in pressure. The volumetric adsorption of the fourth sample of titanium hydrazide was calculated to be about 24 kg/m$^3$. If the isotherm for the fourth sample were extrapolated to a pressure of 200 atm, the fourth sample would have a gravimetric adsorption of 3.75 wt % and a volumetric adsorption of 75 kg/m$^3$.

For both the third sample and the fourth sample, a linear relationship between the pressure and the gravimetric adsorption was observed. An increase in pressure is accompanied by an increase in gravimetric adsorption. Furthermore, complete reversibility of hydrogen adsorption was observed for both the third sample and the fourth sample across the whole range of pressures at room temperature.

EXAMPLE 3

Chromium Hydrazide Materials

Preparation of Chromium Hydrazide Samples

The following procedure was used to prepare a chromium hydrazide sample.

1. $Cr_4[(CH_3)_3SiCH_2]_8$ was reacted with hydrazine at a 1 Cr:1.5 hydrazine ratio in a solution of toluene to form a chromium hydrazide polymer.

2. The chromium hydrazide polymer was filtered to obtain a solid.

3. The solid chromium hydrazide polymer was heated to 100° C. in vacuum.

Hydrogen Adsorption Measurements

A hydrogen adsorption-desorption isotherm for the above-mentioned chromium hydrazide sample was obtained using a computer controlled commercial gas reaction controller. Gravimetric adsorption of the sample can be read from the isotherm. Volumetric adsorption can be calculated from the gravimetric adsorption and the skeletal density. The skeletal density was measured by a pycnometer.

The chromium hydrazide sample was measured by a pycnometer to have a skeletal density of 1.231 g/cm$^3$. The hydrogen adsorption-desorption isotherm for this sample is shown in FIG. 29.

Figure 29:
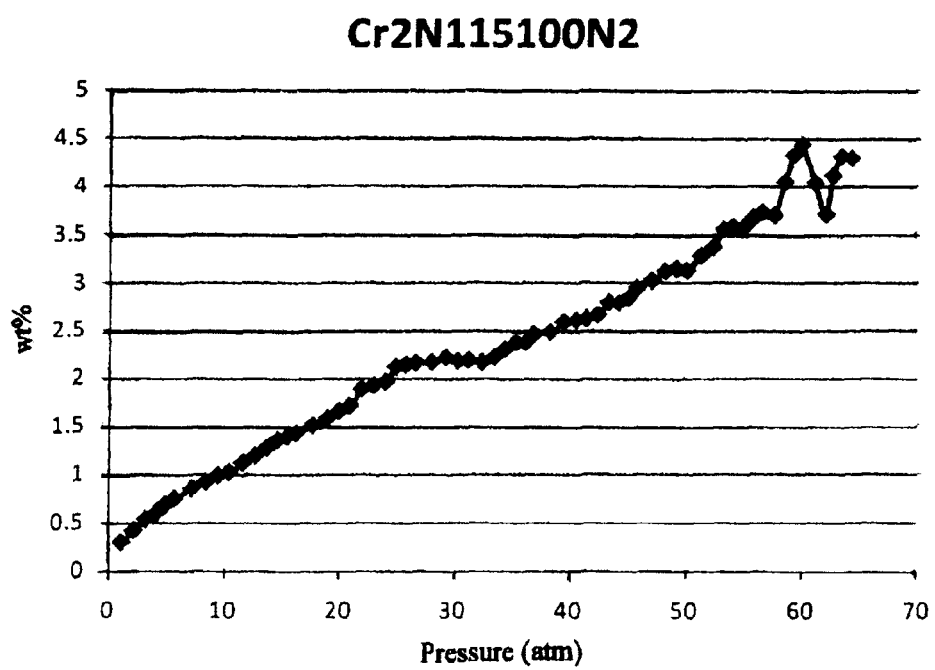
FIG. 29 shows the hydrogen adsorption-desorption isotherm of a preferred chromium hydrazide material.

As shown in FIG. 29, the sample of chromium hydrazide has a gravimetric adsorption of about 4.2 wt % at a temperature of 77 K. The volumetric adsorption of the sample of chromium hydrazide was calculated to be about 51.7 kg/m$^3$ at 77K and 65 bar, and about 8.98 kg/m$^3$ at 298 K and 65 bar.

A linear relationship between the pressure and the gravimetric adsorption was observed. An increase in pressure is accompanied by an increase in gravimetric adsorption. Furthermore, complete reversibility of hydrogen adsorption was observed for the chromium hydrazide sample across the whole range of pressures.

Although this disclosure has described and illustrated preferred embodiments of the invention, it is to be understood that the invention is not restricted to these particular embodiments. Rather, the invention includes all embodiments that are functional or mechanical equivalents of the specific embodiments in features that have been described and illustrated herein. Many modifications and variations will now occur to those skilled in the art. For a definition of the invention, reference is made to the following claims.

We claim:

1. A polymer comprising -[$MN_2$]— as a repeating unit, wherein M is selected from the group consisting of Sc, Ti, V, Cr, Mn, Fe, Co, Zr, Nb, Mo, and mixtures thereof, and wherein the polymer further comprises one or more residual groups.

2. The polymer of claim 1, wherein M is selected from the group consisting of Ti, V, Cr, and mixtures thereof.

3. The polymer of claim 1, wherein the one or more residual groups are present in an amount of 25% by weight of the polymer or less, and preferably 10% by weight of the polymer or less.

4. The polymer of claim 1, wherein the polymer is used for hydrogen storage.

5. The polymer of claim 4, wherein the polymer stores hydrogen by binding $H_2$ to M by a Kubas interaction.

6. The polymer of claim 1, wherein the polymer is used in a sensor, the sensor operates to detect hydrogen in a system.

7. A polymer comprising a repeating unit selected from the group consisting of -[$MN_2$]—, -[$M_2N_3$]—, and mixtures thereof, wherein M is selected from the group consisting of Sc, Ti, V, Cr, Mn, Fe, Co, Zr, Nb, Mo, and mixtures thereof.

8. The polymer of claim 7, wherein the repeating unit comprises -[$M_2$-$N_3$]—.

9. The polymer of claim 8, wherein M is selected from the group consisting of Ti, V, Cr, and mixtures thereof.

10. The polymer of claim 8, wherein the polymer further comprises one or more residual groups.

11. The polymer of claim 10, wherein the one or more residual groups are present in an amount of 25% by weight of the polymer or less and preferably 10% by weight of the polymer or less.

12. The polymer of claim 7, wherein the polymer is used for hydrogen storage.

13. The polymer of claim 12, wherein the polymer stores hydrogen by binding $H_2$ to M by a Kubas interaction.

14. The polymer of claim 7, wherein the polymer is used in a sensor, and the sensor operates to detect hydrogen in a system.

15. A method of producing a polymer, said method comprising:
 (i) reacting M with R to produce compounds selected from the group consisting of $MR_3$, $MR_4$, and mixtures thereof, wherein M is selected from the group consisting Sc, Ti, V, Cr, Mn, Fe, Co, Zr, Nb, Mo, and mixtures thereof, and R is a sterically demanding group or a group that protects a low coordination number for M; and
 (ii) reacting the compounds selected from the group consisting of $MR_3$, $MR_4$, and mixtures thereof with hydrazine in an inert atmosphere to produce a polymer comprising repeating units selected from the group consisting of -[$MN_2$]—, -[$M_2N_3$]—, and mixtures thereof, and wherein the steps of reacting the compounds selected from the group consisting of $MR_3$, $MR_4$, and mixtures thereof with hydrazine is carried out in the presence of a solvent.

16. The method of claim 15, wherein M is selected from the group consisting of Ti, V, Cr, and mixtures thereof.

17. The method of claim 15, wherein the sterically demanding group is selected from the group consisting of an alkyl group, an alkenyl group, an alkynyl group, and an amido group.

18. The method of claim 17, wherein the alkyl group comprises 1 to 8 carbon atoms.

19. The method of claim 17, wherein the sterically demanding group is an amido group.

20. The method of claim 15, wherein the group that protects a low coordination number for M is selected from the group consisting of an aryl group, an ether group, and an alkenyl group.

21. The method of claim 15, wherein the group that protects a low coordination number for M is selected from the group consisting of a phenyl group, a benzyl group, a tolyl group, a xylyl group, naphthyl group, tetrahydrofuran an alkyl group and a mesityl group.

22. The method of claim 15, wherein R is selected from the group consisting of bis(trimethylsilyl)methyl and pentylene.

23. The method of claim 15, wherein $MR_3$ is selected from the group consisting of trismesitylvanadium, tribenzyltitanium, tris [bis(trimethylsilyl)methyl]titanium, and trispentylenetitanium.

24. The method of claim 15, wherein $MR_4$ is selected from the group consisting of V(mesityl)$_3$.tetrahydrofuran and tetrabenzyltitanium.

25. The method of claim 15, wherein the inert atmosphere is free of oxygen.

26. The method of claim 15, wherein the solvent is a hydrocarbon solvent selected from the group consisting of benzene, kerosene, toluene, and xylene.

27. The method of claim 15, wherein the step of reacting the compounds selected from the group consisting of $MR_3$, $MR_4$, and mixtures thereof with hydrazine is carried out at a temperature of 0° C. to 300° C.

28. The method of claim 15, wherein the step of reacting the compounds selected from the group consisting of $MR_3$, $MR_4$, and mixtures thereof with hydrazine is carried out at a temperature of 50° C. to 200° C., and preferably 100° C. to 200° C.

29. The method of claim 15, wherein the step of reacting the compounds selected from the group consisting of $MR_3$, $MR_4$, and mixtures thereof with hydrazine is carried out at a pressure of 1 atm to 10 atm.

30. A method of producing a polymer, said method comprising:
 (i) reacting Cr with $(CH_3)_3SiCH_2$ to produce $Cr_4[(CH_3)_3SiCH_2]_8$ and
 (ii) reacting $Cr_4[(CH_3)_3SiCH_2]_8$ with hydrazine to produce a polymer, the polymer comprising repeating units selected from the group consisting of —[$CrN_2$]—, —[$Cr_2N_3$]—, and mixtures thereof.

31. A method of storing hydrogen in a system, said method comprising:
 (i) providing a polymer in the system, wherein the polymer comprises repeating units selected from the group consisting of -[$MN_2$]—, -[$M_2N_3$]—, and mixtures thereof, wherein M is selected from the group consisting Sc, Ti, V, Cr, Mn, Fe, Co, Zr, Nb, Mo, and mixtures thereof;
 (ii) adding hydrogen to the system; and
 (iii) allowing the hydrogen to bind with the polymer.

32. The method of claim 31, wherein M is selected from the group consisting of Ti, V, Cr, and mixtures thereof.

33. The method of claim 31, wherein the hydrogen binds with M by a Kubas interaction.

34. The method of claim 31, wherein the system is substantially free of oxygen.

35. The method of claim 31, the step of adding hydrogen to the system increases hydrogen pressure in the system to 50 atm to 200 atm.

36. The method of claim 35, further comprising after the step of adding hydrogen, a step of releasing the hydrogen pressure in the system to release the hydrogen from the polymer.

37. A system for storing hydrogen, the system comprising a storage tank and a polymer inside the storage tank, wherein the polymer comprises repeating units selected from the group consisting of -[$MN_2$]—, -[$M_2N_3$]—, and mixtures thereof, wherein M is selected from the group consisting Sc, Ti, V, Cr, Mn, Fe, Co, Zr, Nb, Mo, and mixtures thereof.

38. The system of claim 37, wherein M is selected from the group consisting of Ti, V, Cr, and mixtures thereof.

39. The system of claim 37, wherein the storage tank comprises one or more openings in a wall of the storage tank, wherein fluids can pass into the storage tank or out of the storage tank through said one or more openings, and one or more valves which control the passage of fluids through the one or more openings.

\* \* \* \* \*